(12) United States Patent
Ellis et al.

(10) Patent No.: US 8,327,864 B2
(45) Date of Patent: Dec. 11, 2012

(54) FLOW CONTROLLER

(75) Inventors: Michael R. Ellis, Yorba Linda, CA (US); David L. Goodale, Yorba Linda, CA (US); Brian R. Jarrett, Tehachapi, CA (US)

(73) Assignee: Coast Pneumatics, Inc., Anaheim, CA (US)

( * ) Notice: Subject to any disclaimer, the term of this patent is extended or adjusted under 35 U.S.C. 154(b) by 241 days.

(21) Appl. No.: 12/903,998

(22) Filed: Oct. 13, 2010

(65) Prior Publication Data

US 2011/0083748 A1   Apr. 14, 2011

Related U.S. Application Data

(60) Provisional application No. 61/251,262, filed on Oct. 13, 2009.

(51) Int. Cl.
*F16K 1/52* (2006.01)
*F15D 1/00* (2006.01)

(52) U.S. Cl. .................. 137/1; 137/625.15; 137/625.41; 137/553; 251/208

(58) Field of Classification Search ............. 137/625.15, 137/625.41, 553, 601.16, 601.19, 1; 251/208
See application file for complete search history.

(56) References Cited

U.S. PATENT DOCUMENTS

| | | | |
|---|---|---|---|
| 2,911,008 A | 4/1956 | DuBois | |
| 3,341,168 A | 9/1967 | Toeppen | |
| 4,011,893 A | 3/1977 | Bentley | |
| 4,067,935 A | 1/1978 | Jones et al. | |
| 4,471,805 A | 9/1984 | Solie et al. | |
| 4,475,573 A | 10/1984 | Hindman | |
| 4,544,130 A | 10/1985 | Stoll et al. | |
| 4,946,134 A | 8/1990 | Orlandi | |
| 4,947,891 A | 8/1990 | Genbauffe | |
| 5,370,154 A | 12/1994 | Greer | |
| 5,927,337 A | 7/1999 | LaMantia | |
| 5,988,203 A | 11/1999 | Hutton | |
| 6,374,859 B1 | 4/2002 | Vu et al. | |
| 6,726,175 B1 | 4/2004 | Saba et al. | |
| 7,628,170 B2 * | 12/2009 | Kok-Hiong et al. | 137/601.2 |
| 8,074,678 B2 * | 12/2011 | Kee et al. | 251/208 |
| 2001/0003289 A1 | 6/2001 | Mead et al. | |
| 2006/0070663 A1 | 4/2006 | Schmitt | |
| 2006/0283514 A1 | 12/2006 | Rehder et al. | |
| 2008/0066818 A1 | 3/2008 | Nicolini | |
| 2009/0057590 A1 | 3/2009 | Kok-Hiong et al. | |
| 2009/0090415 A1 | 4/2009 | Harris et al. | |
| 2009/0255596 A1 | 10/2009 | Leys | |

* cited by examiner

*Primary Examiner* — Kevin Lee
(74) *Attorney, Agent, or Firm* — Knobbe, Martens, Olson & Bear, LLP

(57) ABSTRACT

A movable flow controller is interposed in a fluid flow path. The flow controller includes an elongate groove having a first end and a second end. The groove preferably is sized and shaped so that a cross-sectional area of the groove changes along its length from the first end to the second end, and terminates in a hole through the flow controller. In operation, a portion of the groove is aligned with an inlet of the flow path on a first side of the controller, and the hole is in communication with an outlet of the flow path on a second side of the controller. Moving the flow controller relative to the flow path input varies the minimum cross-sectional area of the flow path through the controller and thus selectively limits fluid flow through the controller.

18 Claims, 17 Drawing Sheets

FLOW CONTROLLER

CROSS-REFERENCE TO RELATED APPLICATIONS

This application claims priority to U.S. Application No. 61/251,262, filed Oct. 13, 2009, titled FLOW CONTROLLER, the entire contents of which are incorporated by reference herein and made a part of this specification.

BACKGROUND

1. Field of the Invention

This disclosure relates to fluid control devices and in particular relates to devices used to control flow between a fluid input and a fluid output.

2. Description of the Related Art

Fluid flow systems where fluid flow rate needs to be precisely controlled are required in many health and industrial applications. For example, a fluid flow system may be used in a ventilator system used to administer oxygen mixed with air for a controllable breathing mixture for patients requiring breathing assistance. It is vital that a correct oxygen/air mixture is used to prevent oxygen toxicity. It is well known that elevated partial pressures of oxygen may result in cell damage and death.

Generally needle valve assemblies have been used to precisely control the fluid flow between a fluid input and a fluid output. Needle valves are costly and difficult to manufacture due to stringent machining requirements and the high degree of precision required. A needle valve is required to control the fluid flow at each valve station. Each valve station must be wider than would otherwise be required in order to accommodate the needle valve hardware. The needle valve is mounted directly to the manifold. In order to mount the needle valve assembly, the manifold needs to be precisely machined and assembled. The needle must fit concentric to the opening in the manifold and must enter the inlet flow path at right angles. If the needle is threaded in too far it will bend or break, often the operator is unaware of the damage. Additionally it is nearly impossible to completely shut off the flow because of a round needle entering a round flow path at right angles.

SUMMARY

Accordingly there is a need in the art for a flow control system that precisely controls fluid flow, can be quickly and precisely adjusted, can accommodate multiple valves spaced closely together, and/or can be modified without requiring the expense and complexity of additional hardware and remanufacturing of the manifold.

In accordance with one embodiment, the present invention provides a flow controller, comprising a body having a first side and a second side. An elongate groove is formed on the first side of the body, the groove having a first end and a second end. A cross-sectional area of the groove increases from the second end toward the first end. A hole is formed through the body at the first end of the groove, the hole extending to the second side of the body.

In some such embodiments, a flow control system employs such a flow controller interposed in a flow path. In one embodiment, the flow controller is interposed between a valve and a manifold.

In another embodiment, a method of controlling fluid flow comprises arranging such a flow controller in a flow path. In some embodiments the method includes interposing the flow controller between a valve and a manifold.

In one such embodiment, the groove is continuously tapered in width and depth, such that at the first end the groove is widest and deepest, and at the second end the groove terminates at a point where it becomes generally flush with the body. In another embodiment the flow controller, wherein the body is generally circular and the groove is arcuate.

In another embodiment the body further comprises a first section having a first diameter and a first thickness, and a second section having a second diameter and a second thickness. The first diameter and second diameter are different, and the first thickness and second thickness are different. In a further embodiment the second section has a plurality of lobes formed circumferentially about the second section. In yet another embodiment at least one of the plurality of lobes has a marking corresponding to a position on the groove.

In a still further embodiment the groove has a profile that is substantially semi-circular.

In some embodiments the body further comprises at least one annular groove configured to accommodate a sealing member.

In yet another embodiment the body is circular and the groove is generally arcuate about an axis of the body. In one such embodiment there is an angular space on the first side between the first end and the second end of the groove that is substantially flat, wherein the space is approximately 90 degrees. In one such embodiment the angular space is a different material than the rest of the flow controller, wherein the material is an elastomeric material.

In still another embodiment, the flow controller further comprises a center hole in the center of the body that extends from the first face to the second face, wherein the second hole is configured to accommodate a valve stud.

In accordance with another embodiment, the present invention provides a flow control system. The system includes a manifold comprising a fluid inlet, a valve and a flow controller. The flow controller comprises a body having a first side and a second side, an elongate groove on the first side of the body, the groove having a first end and a second end. A cross-sectional area of the groove increases from the second end toward the first end. A hole is formed through the body at the first end of the groove, the hole extending to the second side of the body. The flow controller is disposed between the valve and manifold, and a fluid flow path conveys a fluid from the manifold through the fluid inlet, the flow controller, and to the valve. The flow controller is movable relative to the manifold from a first position in which a first portion of the groove is aligned with the fluid inlet to a second position in which a second portion of the groove is aligned with the fluid inlet. The cross-sectional area of the groove at the first portion determines a first flow rate when the flow controller is in the first position and the cross-sectional area of the groove at the second portion determines a second flow rate when the flow controller is in the second position. The first flow rate is different than the second flow rate.

In one such embodiment substantially all of the fluid flow passes through the hole in the flow controller.

Another such embodiment further comprises a valve stud adapter having a valve engagement region and a manifold engagement region, wherein the valve engagement region couples to the valve and the manifold engagement region couples to the manifold.

In another embodiment the flow controller is movable relative to the manifold so that the fluid inlet is not aligned with the groove, and flow is substantially blocked by the flow controller.

In accordance with still another embodiment, a method of controlling fluid flow in a manifold is provided. The method includes providing a manifold having a fluid inlet and a fluid outlet; providing a valve; and providing a flow controller having a body, an elongate groove having a first end and a second end. The cross-sectional area of the groove increases from the second end to the first end. There is a hole in the body of the flow controller, wherein the hole is adjacent the first end. The method further includes supplying a fluid to the manifold, wherein a fluid flow path conveys the fluid from the manifold through the fluid inlet, the flow controller, the valve, and to the fluid outlet. The method additionally comprises moving the flow controller relative to the manifold to a first position in which a first portion of the groove is aligned with the fluid inlet. The fluid flows at a first fluid flow rate from the fluid inlet to the fluid outlet. The method additionally comprises moving the flow controller relative to the manifold to a second position in which a second portion of the groove is aligned with the fluid inlet. The fluid flows at a second fluid flow rate from the fluid inlet to the fluid outlet and the first fluid flow rate is different than the second fluid flow rate.

In one embodiment the method further comprises moving the flow controller relative to the manifold so that the fluid inlet is aligned substantially with the hole in the flow controller. The fluid flows at a third flow rate from the fluid inlet to the fluid outlet. In another embodiment the method further comprises moving the flow controller relative to the manifold so that the fluid inlet is not aligned with the groove, and the fluid is substantially blocked by the flow controller.

In accordance with a preferred embodiment, a flow controller comprises a base, a through hole, and a variable groove. At a first end the groove is widest and deepest and at a second end the groove is flush with the base. The flow controller is used in conjunction with an inlet fluid flow, for example a valve, and some type of outlet, for example a manifold. The flow controller couples with the inlet and the outlet such that it is interposed between the two, and remains in constant fluid communication with the inlet and the outlet when manipulated. The fluid flow will flow from the inlet (source) through the flow controller and to the outlet. When the through hole of the flow controller is aligned with the fluid inlet, resistance is minimized and the flow will be at its maximum flow for the flow controller. The maximum flow of the flow controller does not have to be the maximum flow of the fluid inlet source. When the flow controller is manipulated the inlet will no longer be directly aligned with the through hole, but will align with a portion of the variable groove. Manipulation of the controller further varies alignment of the inlet along the groove from the through hole toward the second end. With this changing alignment, the flow passage will decrease, and fluid flow will correspondingly decrease. When the flow controller is manipulated so that the inlet is aligned with a portion of the flow controller beyond the second end of the groove, the inlet is flush with the base and flow is nearly nonexistent.

In accordance with still another embodiment, a method of controlling fluid flow in a manifold comprises providing a manifold having a fluid inlet and a fluid outlet, providing a valve and providing a flow controller having a body and an elongate groove having a first end and a second end. A cross-sectional area of the groove increases from the second end toward the first end, and a hole extends through the body adjacent the first end of the groove. In the method fluid is supplied to the manifold, and a fluid flow path conveys the fluid from the manifold through the fluid inlet, the flow controller, the valve, and to the fluid outlet. The method includes moving the flow controller relative to the manifold from a first position in which a first portion of the groove is aligned with the fluid inlet to a second position in which a second portion of the groove is aligned with the fluid inlet. The fluid flows at a first fluid flow rate from the fluid inlet to the fluid outlet when the flow controller is in the first position and the fluid flows at a second fluid flow rate from the fluid inlet to the fluid outlet when the flow controller is in the second position. The first fluid flow rate is different than the second fluid flow rate.

One such method further comprises moving the flow controller relative to the manifold so that the fluid inlet is aligned substantially with the hole in the flow controller, and fluid flows at a third flow rate from the fluid inlet to the fluid outlet, and the third flow rate is a maximum flow rate through the flow controller.

Another such method further comprises moving the flow controller relative to the manifold to a fourth position in which the fluid inlet is not aligned with the groove, and wherein the fluid flow is substantially blocked by the flow controller when the controller is in the fourth position.

DETAILED DESCRIPTION OF PREFERRED EMBODIMENTS

Figure 1:
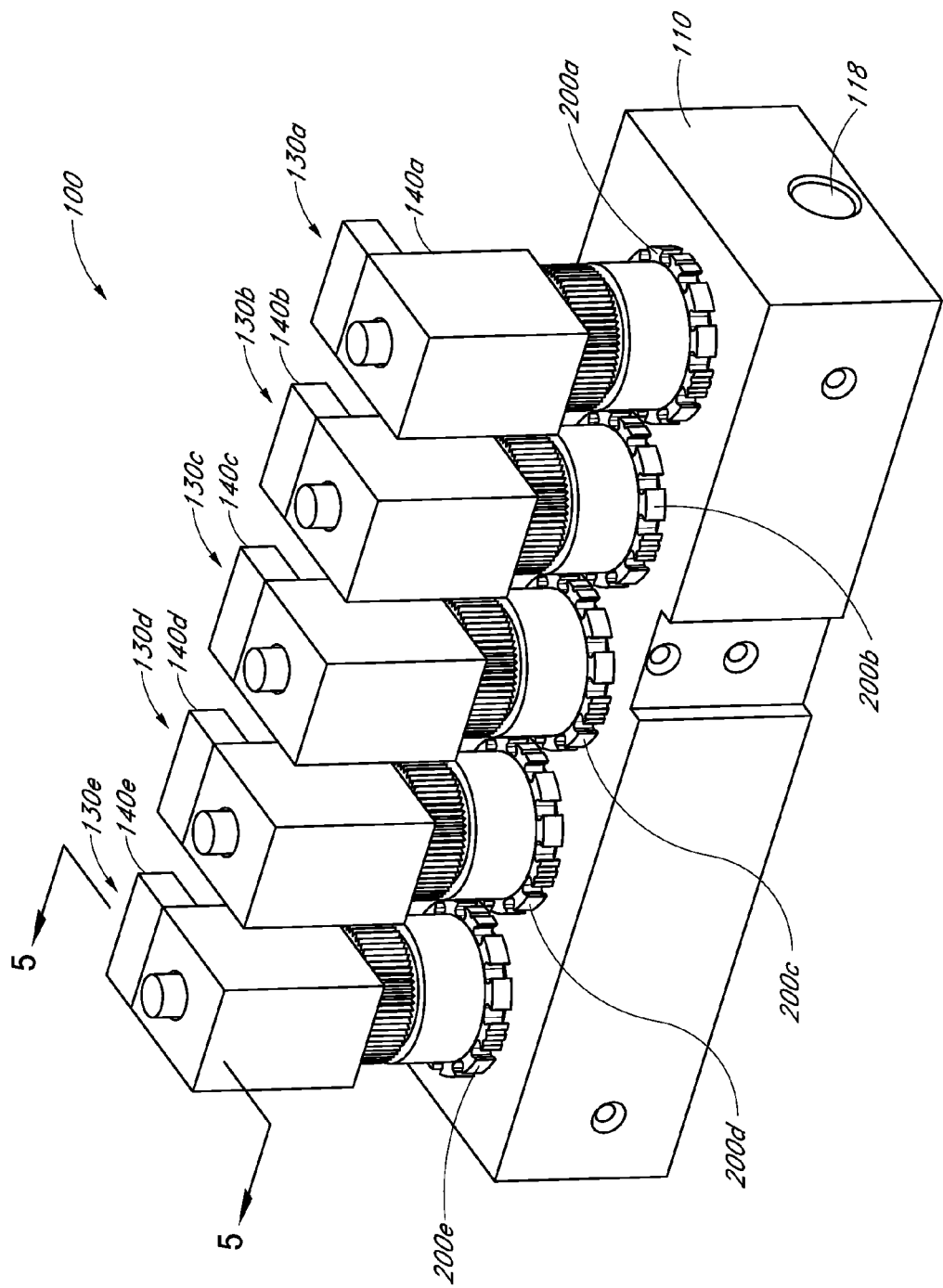
FIG.1 is a perspective view of one embodiment of a flow control system.
Figure 4A:
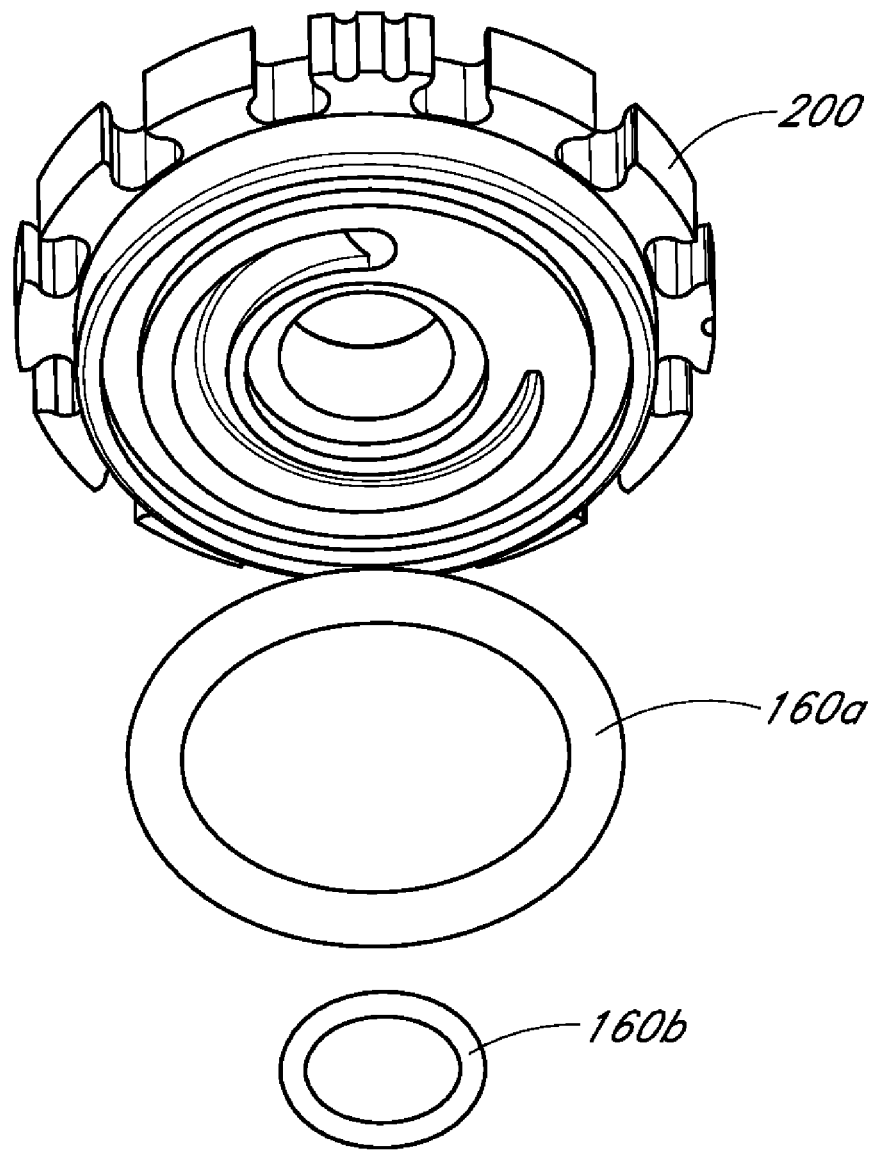
FIG.4A is an exploded view of the flow controller of FIGS. 2A-2C and associated seals.
Figure 4B:
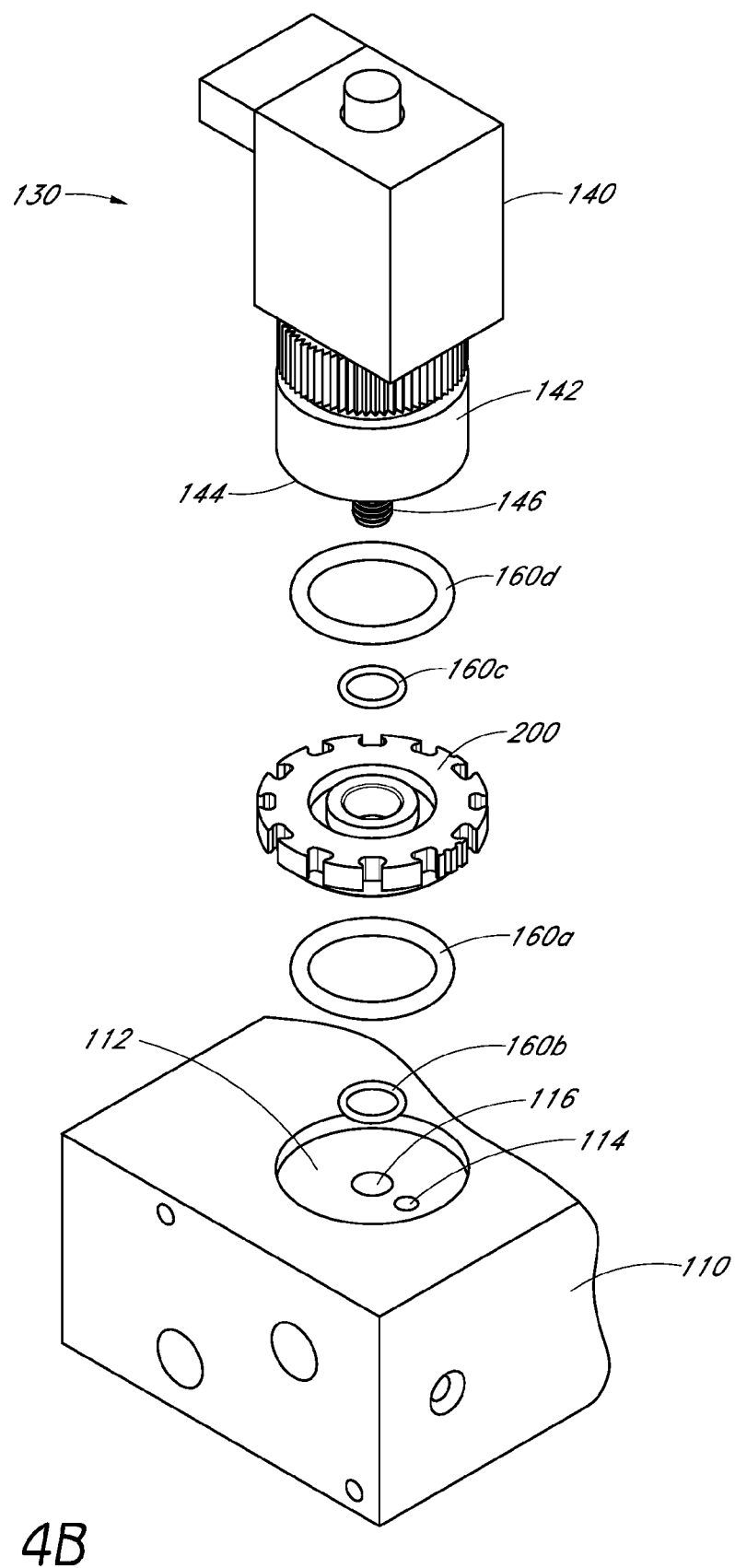
FIG.4B is an exploded view of one valve station of the flow control system of FIG.1.
Figure 5:
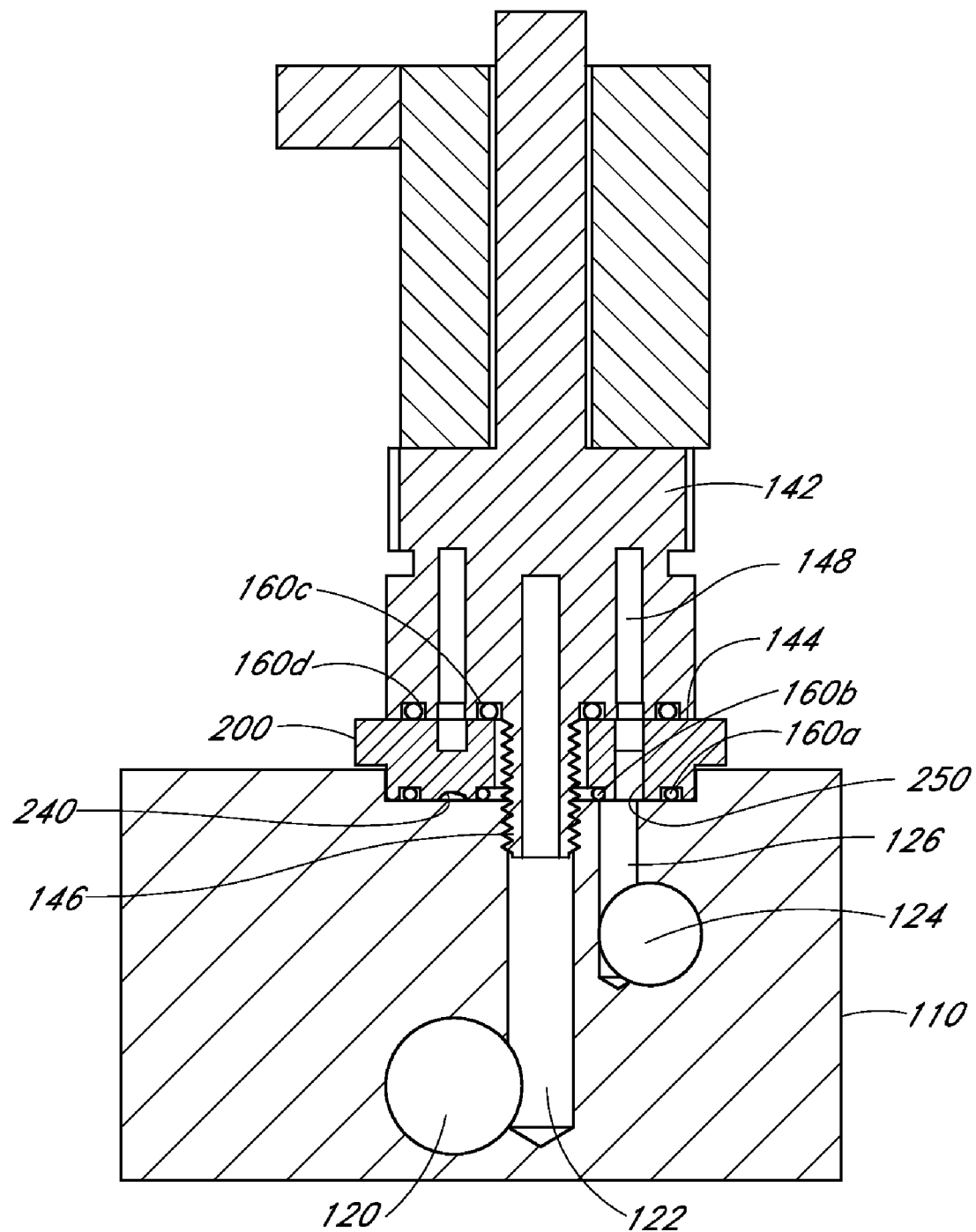
FIG.5 is a cross section of a valve station from the flow control system of FIG.1 taken along line 5-5.

With initial reference to FIGS. 1, 4, and 5, an embodiment of a fluid flow control system 100 is shown. The fluid flow control system can be used with various manifolds, controllers, fluids, blender modules and the like. The illustrated fluid flow control system 100 is presented herein as an example to aid in describing principles and structures in accordance with several embodiments. It is understood that fluid flow control systems having a different appearance or differences in specific structure may still employ one or more of the principles discussed herein.

The illustrated flow control system 100 comprises a manifold 110, and a plurality of valve stations 130*a-e*. The valve stations have a plurality of valves 140*a-e* and a plurality of flow controllers 200*a-e*. Preferably, the system is configured to meet a specific application with specific valves and flow controllers. For example, each valve station may be configured to handle different fluids, different fluid flow rates, and different valves. In some embodiments, all of the valve stations will be connected to a controller board that controls the operation of the valves. The controller board operates the valves 140 in order to control the mixture of fluids, which may include gases, such as air and oxygen, sent through the manifold outlet 118. In some embodiments the manifold 100 is connected to a blender module which supplies the fluid mixture at a specified pressure and flow at the manifold outlet 118.

With additional reference to FIGS. 4B and 5, the illustrated valve stations are comprised of a valve 140, a flow controller 200, and a plurality of sealing members 160, such as elastomeric o-rings. Preferably the sealing members 160 are configured to isolate the flow path between the valve 140 and the manifold 110 from ambient air. In operation fluid from an inlet galley 124 of the manifold 110 flows through the valve 140 and to an outlet galley 120 of the manifold 110. The flow controller 200 is positioned between the manifold and the valve body. Preferably the flow controller controls the fluid flow rate into the valve and the valve controls when fluid flows from the fluid inlet to the fluid outlet. As will be discussed in more detail below, the flow controller 200 can be configured to handle many different applications, and the fluid flow control system 100 may be configured to isolate and mix multiple fluid flows as desired.

Figure 2A:
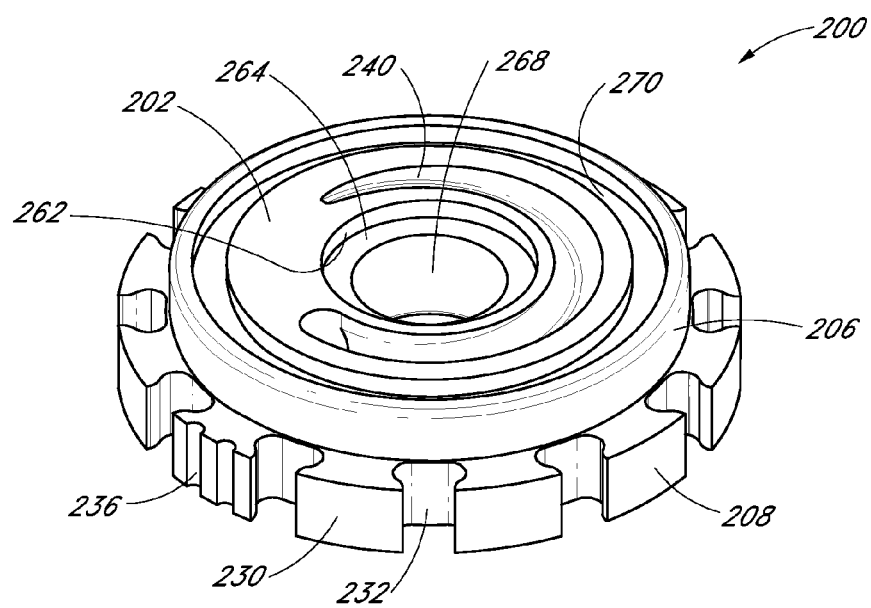
FIG.2A is a perspective view of one embodiment of a flow controller.
Figure 2B:
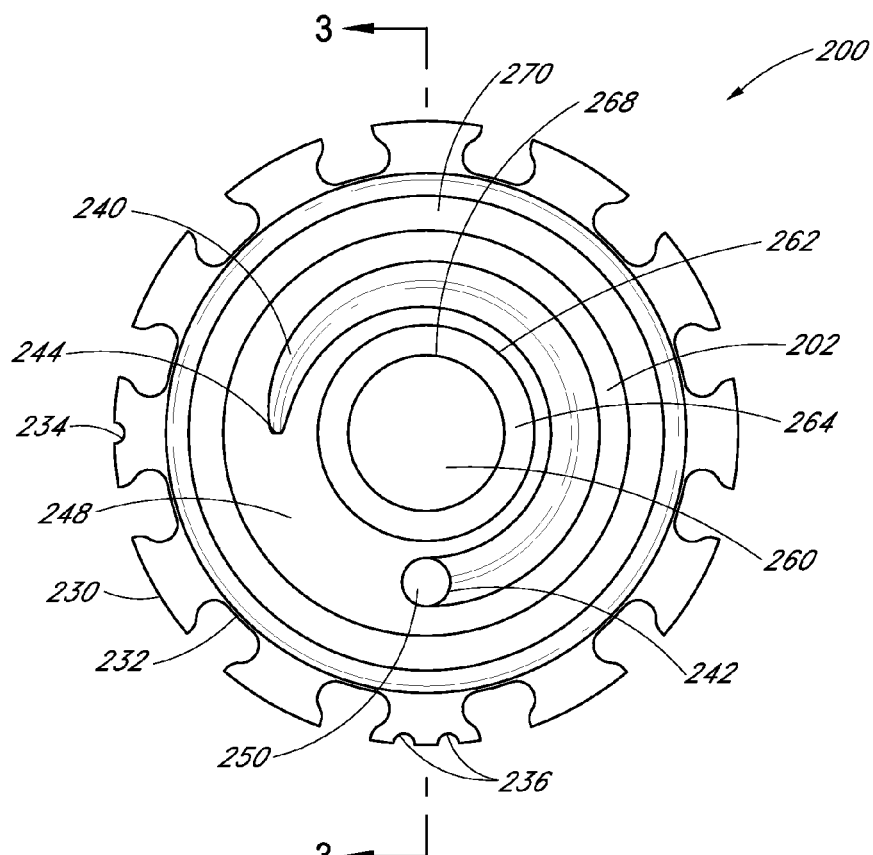
FIG.2B is a front view of one embodiment of the flow controller of FIG. 2A.
Figure 2C:
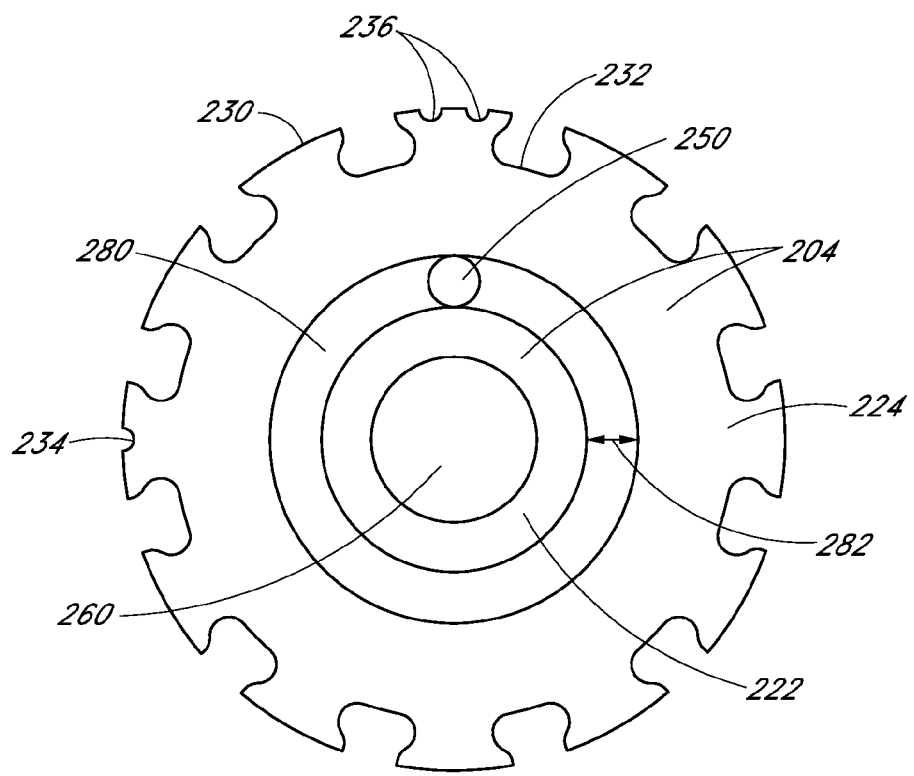
FIG.2C is a back view of one embodiment of a flow controller of FIG. 2A.
Figure 3:
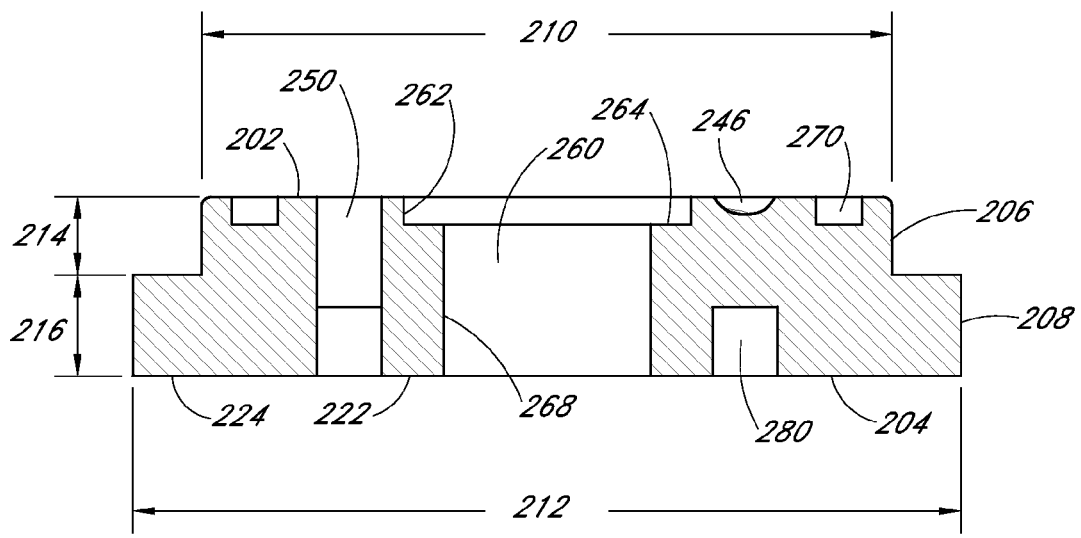
FIG.3 is a cross-section of the flow controller of FIG.2B taken along lines 3-3.

With reference next to FIGS. 2A through 2C and 3, an embodiment of a flow controller 200 is illustrated. The flow controller 200 comprises a body that has a first face 202 and an opposing second face 204. A view of the first face 202 is illustrated in FIG. 2B and a view of the second face 204 is illustrated in FIG. 2C. A cross section of the flow controller is illustrated in FIG. 3.

The flow controller 200 has a generally circular shape with a plurality of regions of varying widths and thickness. In this embodiment there is a first region 206 having a width 210 and thickness 214; and a second region 208, having a width 212 and thickness 216. The outer wall 218 of the first region 206 is substantially smooth; and maintains a substantially constant thickness 214 and width 210, which extends substantially between the first face 202 and the second region 208.

In this embodiment, the second region 208 is wider than the first region 206, resulting in a step-type structure where the regions meet. The second region 208 has a plurality of lobes 230. In this embodiment, the lobes are substantially identical and maintain the generally circular shape of the flow controller. In this embodiment the lobes also have an inward shaped cavity 232 that extends substantially to the width of the first section 212. In some embodiments, the plurality of lobes 230 may be a substantially different shape, and the inward cavity 232 may not extend substantially to the width of the first section 212. In some embodiments, each lobe may not be substantially identical. In other embodiments the outer wall of the second region may be made up of a plurality of small ridges or the outer wall may be substantially smooth, similar to the first region. In other embodiments the first and second regions may have the same width, effectively resulting in a single region extending between the first and second faces. Preferably, the lobes 230 are configured to facilitate manipulation of the flow controller when it is assembled as part of a flow control system, similar to the system illustrated in FIG. 1.

The flow controller 200 further comprises a first annular groove 270, a second annular groove 280, a variable groove 240, a through hole 250, and a mounting hole 260. The first annular groove 270 extends inwardly from the first face 202. In the illustrated embodiment, the first annular groove 270 is substantially the same depth along the whole length of the groove. Preferably, the first annular groove is sized and configured such that a sealing member 160, such as an o-ring, can be seated within the groove.

The second annular groove 280 extends inwardly from the second face 204 and is substantially the same depth along the whole length of the groove. The second face 204 is divided into an inner region 222 and an outer region 224 by the second annular groove 280. The second annular groove 280 is configured to accommodate an inlet location on a valve.

In this embodiment, the first and second annular grooves 270, 280 are concentric with the center hole 260. The through hole 250 extends substantially through the flow controller 200 body extending from the first face 202 to the second annular groove 280. Preferably the diameter of the through hole 250 is configured to be the same width or smaller than the width 282 of the second annular groove 280.

The variable groove 240 is formed in the first face 202. In this embodiment, the variable groove 240 has a substantially circular shape when viewed at an angle perpendicular to the first face 202 and is concentric with the center hole 260. In this embodiment the variable groove 240 extends approximately ¾ or 270° about the center hole. In other embodiments the angular length of the variable groove may vary as desired. The variable groove 240 has a variable depth and width along the length of the groove. On a first end 242, the variable groove terminates at the through hole 250. The variable groove 240 is widest and deepest at the first end 242 and continuously tapers until it terminates at a second end 244 where it becomes flush with the first face 202. In this embodiment there is approximately 90 degrees of circumference between the first end 242 and the second end 244 where the groove 240 does not extend, which represents a null zone 248. It is to be understood that in other embodiments the groove and null zones can have other arcuate lengths as desired.

In the illustrated embodiment the groove 240 has a semi-circular cross section along its length. In other embodiments, the cross section may be triangular, square, rectangular, or another shape. Preferably, however the groove is configured so that a cross sectional area of the groove continuously increases along its length from the second end 244 to the first end 242.

In this embodiment there are markings on the lobes 230 that correspond to locations on the variable groove 240. A first marking 236 corresponds and is opposite the through hole 250. A second marking 234 corresponds and is opposite to the second end of the variable groove 244. Thus, the first and second markings denote the positions of the first and second ends of the variable groove.

The mounting hole 260 is comprised of a sealing wall 262, a recessed face 264, and an inner wall 272. The sealing wall extends inwardly from the first face 202 and transitions into the recessed face 264, effectively forming a step-type structure. The inner wall 272 extends between the recessed face 254 and the second face 204. The inner wall 272 and sealing wall 262 are generally circular and concentric. The recessed face 264, sealing wall 262, and inner wall 272 are sized and configured such that a sealing member, such as an o-ring, can be seated between the inner wall 272 and the sealing wall 262. The mounting hole 260 is configured to accommodate a threaded valve stud.

With additional reference now to FIG. 4A, the assembly of the flow controller 200 and sealing members 160a-b is discussed. When assembled, the flow controller 200 and the plurality of sealing members 160a-b are coupled together. The first annular groove 270 is configured to accommodate the sealing member 160a. The mounting hole 260 is configured to accommodate the sealing member 160b between the sealing wall 262 and the inner wall 272. The sealing member 160b generally abuts the recessed face 264 and the sealing wall 262 when coupled to the flow controller 200. Preferably the sealing members are elastomeric members of standard sizes and shapes, such as o-rings.

With additional reference now to FIGS. 1, 4B, and 5, the assembly of a valve station 130 is illustrated. The valve station 130 comprises the flow controller 200, valve 140, and manifold 110. In this embodiment of the flow control system 100, each of the valve stations are substantially similar. Other embodiments may employ valves of different sizes and/or shapes.

The portion of the manifold 110 illustrated in FIG. 4B comprises a valve engagement region 112, a valve station inlet 114, and a valve station outlet 116. In this embodiment, the valve engagement region 112 is a surface countersunk into the manifold 110.

The valve station inlet 114 communicates with an inlet passage 126 and an inlet galley 124. The inlet passage 126 and inlet galley 124 are in fluid communication. The inlet galley 124 is in fluid communication with an inlet source that provides a fluid to the inlet galley 124 and in turn provides fluid to the inlet passage 126. In some embodiments each inlet galley may be in fluid communication with a different inlet source. In other embodiments multiple inlet galleys may be in fluid communication with a single inlet source.

The valve station outlet 116 communicates with an outlet passage 122 and an outlet galley 120. The outlet passage 122 and the outlet galley 120 are in fluid communication. The outlet galley 120 is in fluid communication the manifold outlet 128. Preferably, at least a portion of the outlet passage, near the valve engagement region 112, has an internally threaded region, thus defining a female connection. In some embodiments each outlet galley is in fluid communication with the manifold outlet. In other embodiments the outlet galleys may be in fluid communication with other outlets such as a blender module.

The valve comprises a valve body 142, a valve interface 144, a valve stud 146, and a valve inlet 148. The valve interface 144 comprises a plurality of annular grooves designed to accommodate sealing members 160c and 160d. The valve stud 146 extends outwards from the valve interface 144. The valve stud has an interior cavity that extends from the distal end of the valve stud 146 into the valve body 142 and is in fluid communication with the valve inlet 148. Preferably, the valve stud 146 has an externally threaded region, thus defining a male connection, and defining the valve outlet.

The valve station is assembled by coupling the valve 140, flow controller 200, and manifold 110 together. When the manifold 110 and the flow controller 200 are coupled together, the valve engagement region 112 engages with the first face of the flow controller 202. In some embodiments there may be a gap between the valve engagement region 112 and the first face 202. In the illustrated embodiment the valve stud 146 is configured to threadingly couple with the manifold outlet passage 122. The distal end of the valve stud 146 extends through the mounting hole 260 of the flow controller 200 and protrudes beyond the first face 202. The second face 204 of the flow controller abuts the valve interface 144 when the valve station is assembled. In some embodiments their may be a gap between the second face 204 and the valve interface 144.

The male threaded region of the valve stud 146 engages the female threaded region of the outlet passage 122. Preferably a sealing member, such as Teflon tape, is applied to the threaded region of the valve stud 146 before it is threaded into the manifold outlet passage 122 to help form a seal between the valve 140 and the manifold 110. The valve 140 is then threaded sufficiently tight so that the sealing members 160 form seals between the valve interface 144 and the second face 204 of the flow controller 200, and between the first face 202 of the flow controller 200 and the manifold engagement region 112.

The sealing member 160b creates a seal isolating the valve stud 146 from the inlet passage 126 and further prevents leakage. The sealing member 160a creates a seal isolating the manifold inlet passage 126 and the variable groove 240 from the ambient air and further prevents leakage. The sealing member 160c contacts and creates a seal between the inner region of the second face 222 and valve interface 144. The inner seal isolates the valve stud 146 from the valve inlet 148 and prevents leakage. The sealing member 160d contacts and creates a seal between the outer region of the second face 224 and the valve interface 144. The outer seal isolates the valve inlet 148 from the ambient air and prevents leakage.

When the valve 140, manifold 110 and flow controller 200 are assembled, the variable groove 240 and null zone 248 preferably are aligned with the manifold inlet passage 126 such that the inlet passage 126 is in fluid communication with either the variable groove 240 or the null zone 248 regardless of the angular position of the flow controller 200. Preferably the seals 160a, b cooperate to isolate fluid flow between the inlet port 114 and outlet port 116. The second annular groove 280 preferably is aligned with the valve inlet 148 such that the valve inlet 148 remains in fluid communication with the second annular groove 280 regardless of the angular position of the flow controller 200. Preferably the seals 160c, d cooperate to isolate fluid flow between the inlet port 114 and outlet port 116.

Preferably, the valve 140 is sufficiently tightened onto the manifold 110 to establish a reliable seal, but not to the extent that rotational movement of the flow controller 200 is prevented. Preferably, the flow controller 200 has freedom to rotate about a center axis when urged to do so by a user. However, once in a desired position as set by a user, preferably the fit is sufficiently tight that the flow controller 200 will not rotate on its own accord. Preferably the seals 160 between the flow controller 200, valve 140, and manifold 110 are maintained during such movement. In this embodiment the first region 206 of the flow controller 200 fits into the countersunk portion of the manifold engagement region 112. Preferably the valve engagement region 112 helps secure the position of the valve 140 and flow controller 200 without inhibiting rotational movement of the flow controller.

The operation of the flow controller 200 is described with particular reference to FIG. 5. In this embodiment of the flow control system 100, the flow controller 200 precisely meters fluid flow from an inlet source to the outlet galley 120. In FIG. 5 the flow controller 200 is shown in the orientation that provides maximum fluid flow rate, in which the through hole 250 is inline with the inlet passage 126. When the valve is opened the fluid flows from the inlet passage 126 through the through hole 250 to the valve inlet 148. The fluid then flows through the valve, down through the cavity of the valve stud 146, and into the outlet passage 122 where it feeds into the fluid stream through the outlet galley 120. In some embodiments the maximum fluid flow rate is determined by the size of the through hole.

Rotating the flow controller 200 from the maximum flow position will cause the flow rate to be reduced. As the flow controller is rotated, the inlet passage 126 is aligned with an ever decreasing cross section 246 of the variable groove 240. As the cross section 246 decreases the rate at which fluid can flow from the inlet passage 126 into the valve inlet 148 decreases. The flow rate continues to decrease as the flow controller is rotated until the flow controller is rotated past the second end 244 of the variable groove 240. The flow rate decreases in proportion to the decrease in size of the cross section of the variable groove 240. When the flow controller is rotated into the null zone 248, the flow rate is at its minimal state and preferably is substantially blocked. In some embodiments the fluid flow rate is very low or close to zero when the inlet passage 126 is aligned with the null zone 248. Preferably there is no fluid flow between the inlet source and the valve inlet 148 when the inlet passage 126 is aligned with the null zone 248.

In use, a user will rotate the flow control until a desired flow rate is achieved. The flow controller 200 is then maintained at the position corresponding to the desired flow rate by the tightness of installation between the valve 140 and manifold 110, by an external locking mechanism engaging the outer region, such as engaging one or more lobes, or by any other mechanism.

Figure 6:
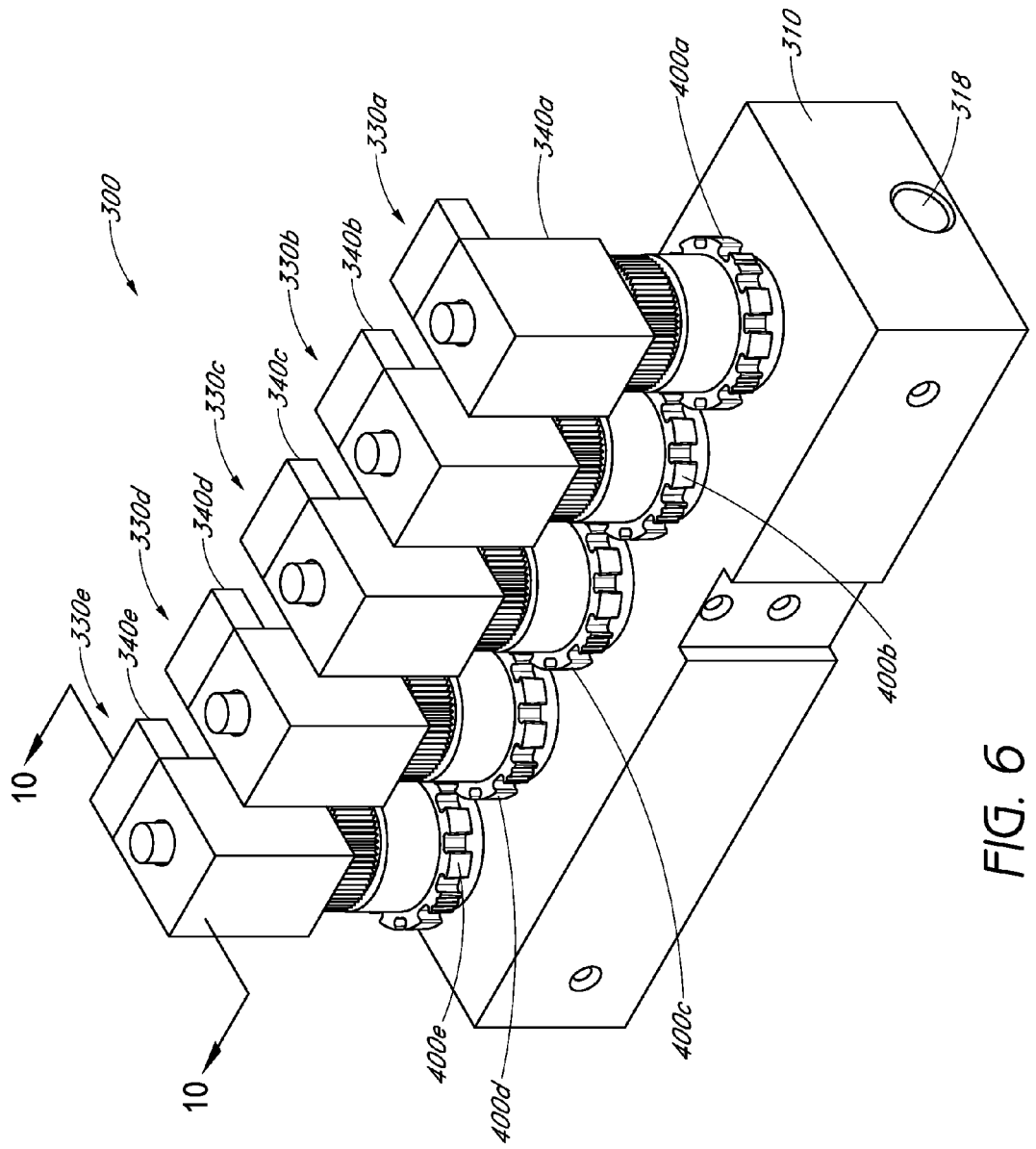
FIG.6 is a perspective view of another embodiment of a flow control system.
Figure 9A:
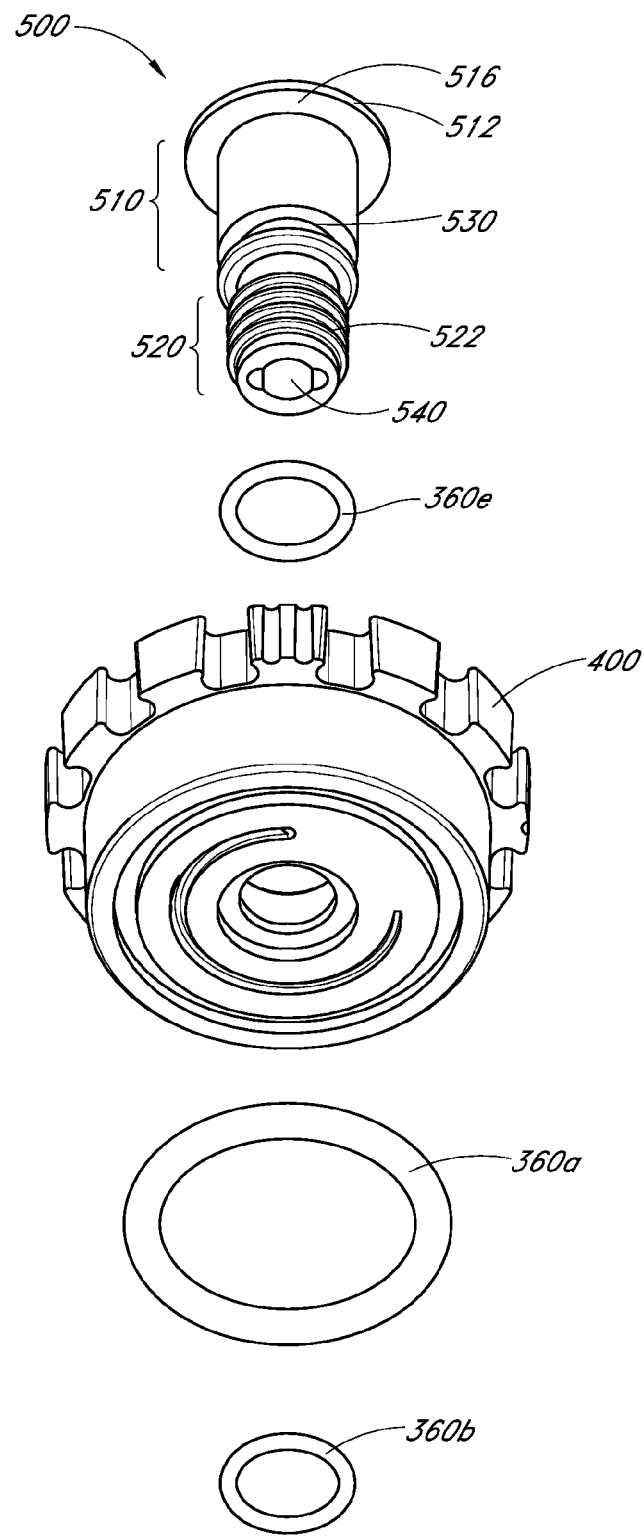
FIG.9A is an exploded view of the flow controller of FIGS. 7A-7C, associated valve spud, and associated seals.
Figure 9B:
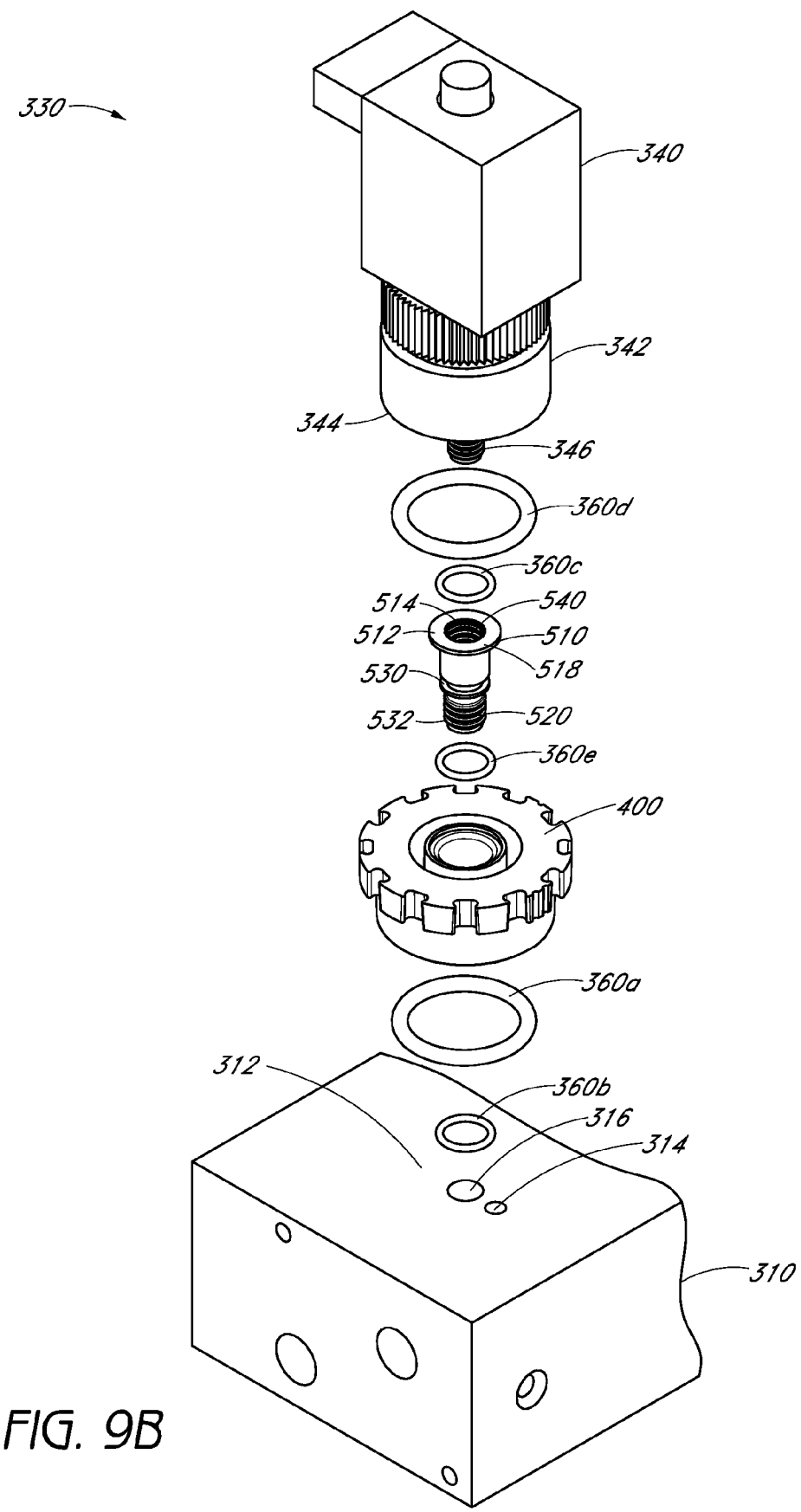
FIG.9B is an exploded view of a valve station of the flow control system of FIG.6.
Figure 10:
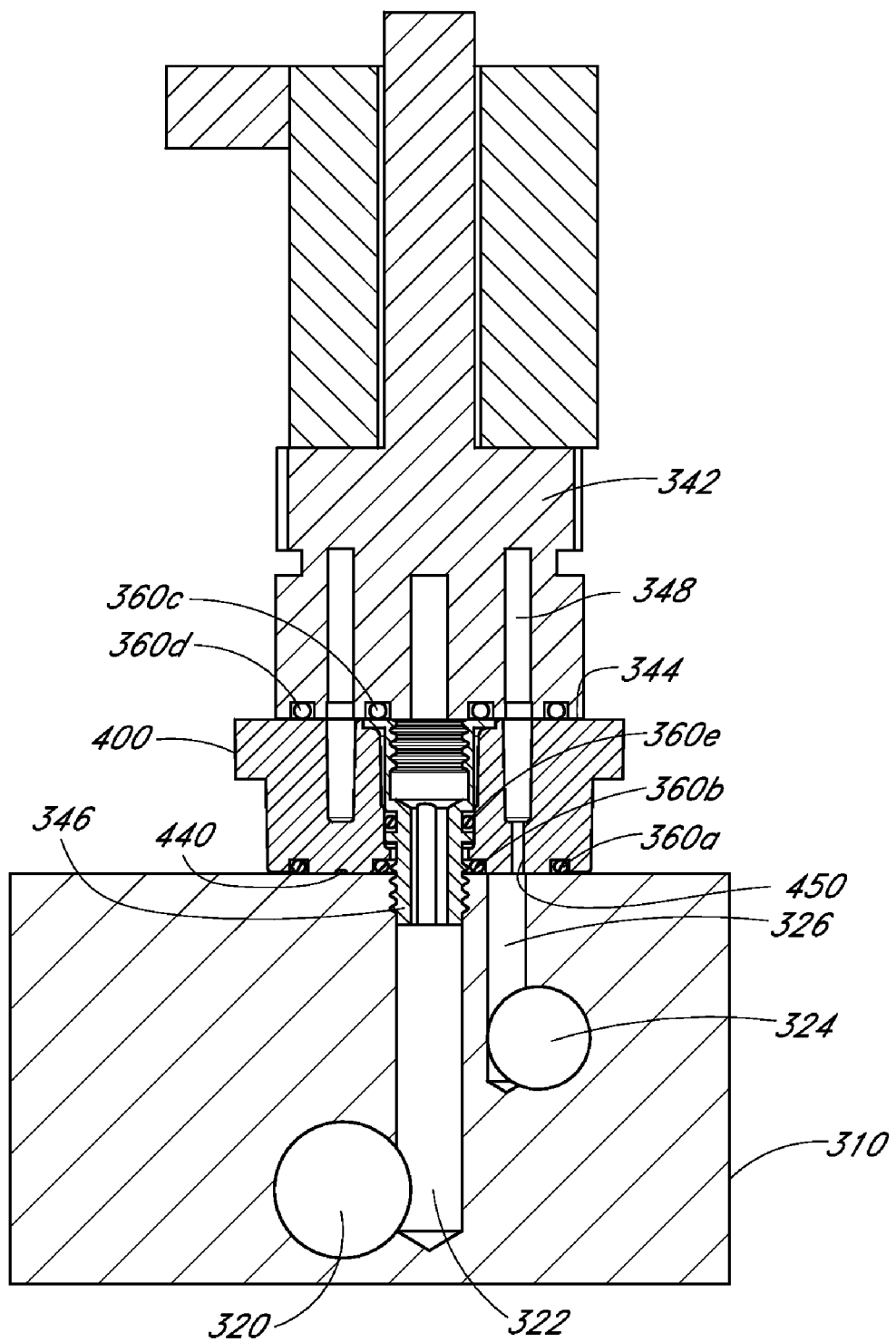
FIG.10 is a cross section of a valve station from the flow control system of FIG.6 taken along lines 10-10.

With reference next to FIGS. 6, 9, and 10, another embodiment of a fluid flow control system 300 is shown. The fluid flow control system can be used with various manifolds, controllers, fluids, blender modules and the like. The illustrated fluid flow control system 300 is presented herein as an example to aid in describing principles and structures in accordance with several embodiments. It is understood that fluid flow control systems having a different appearance or differences in specific structure may still employ one or more of the principles discussed herein.

In this embodiment the flow control system comprises a manifold 310 and a plurality of valves stations 330a-e. The valve stations have a plurality of valves 340a-e and a plurality of flow controllers 400a-e. The flow control system 300 illustrated in FIG. 6 preferably operates following the same general principles described in connection with FIG. 1 detailed above. Additional details related to the components will be discussed in more detail below.

Figure 7A:
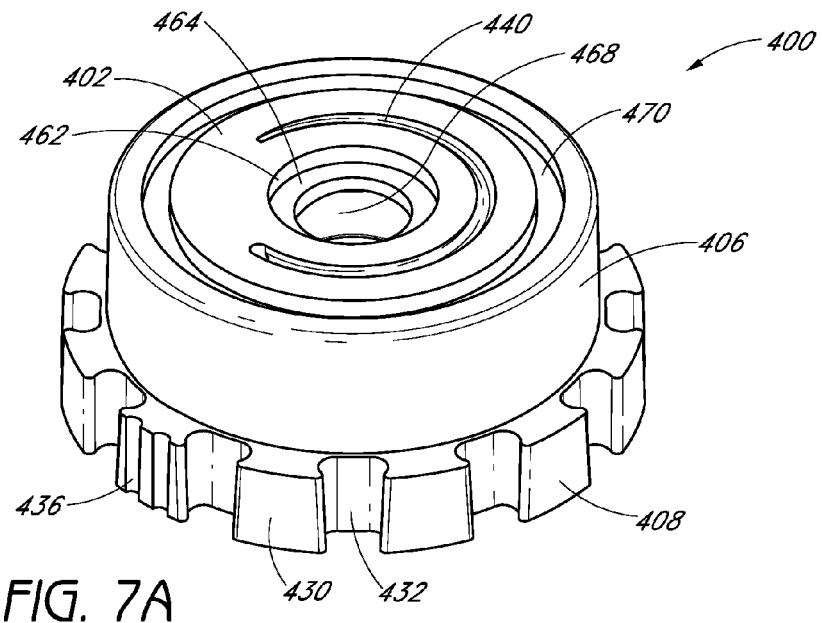
FIG.7A is a perspective view of another embodiment of a flow controller.
Figure 7B:
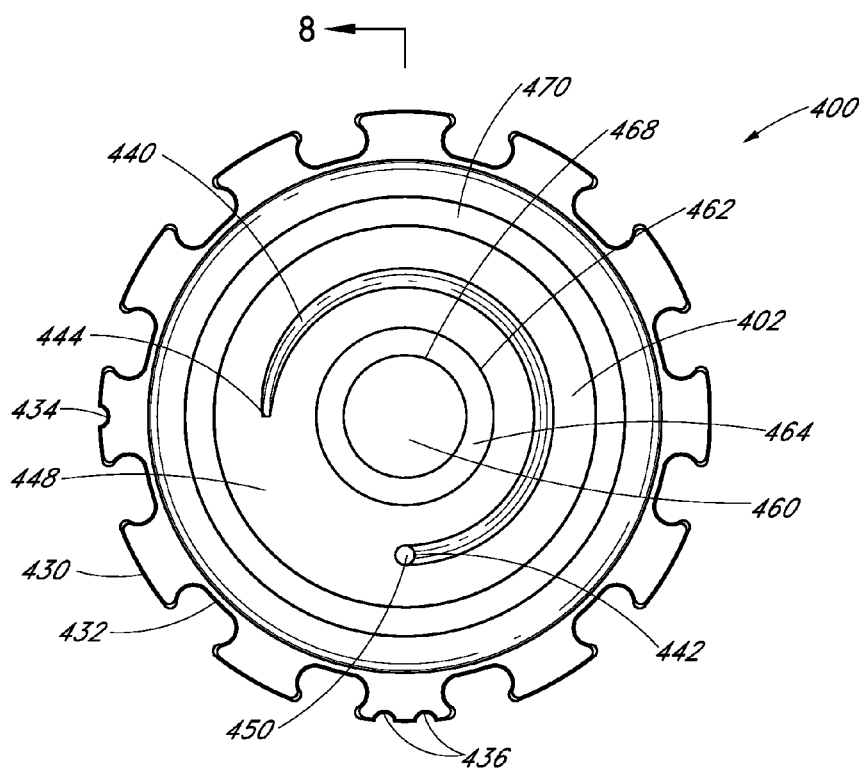
FIG.7B is a front view of the flow controller of FIG.7A.
Figure 7C:
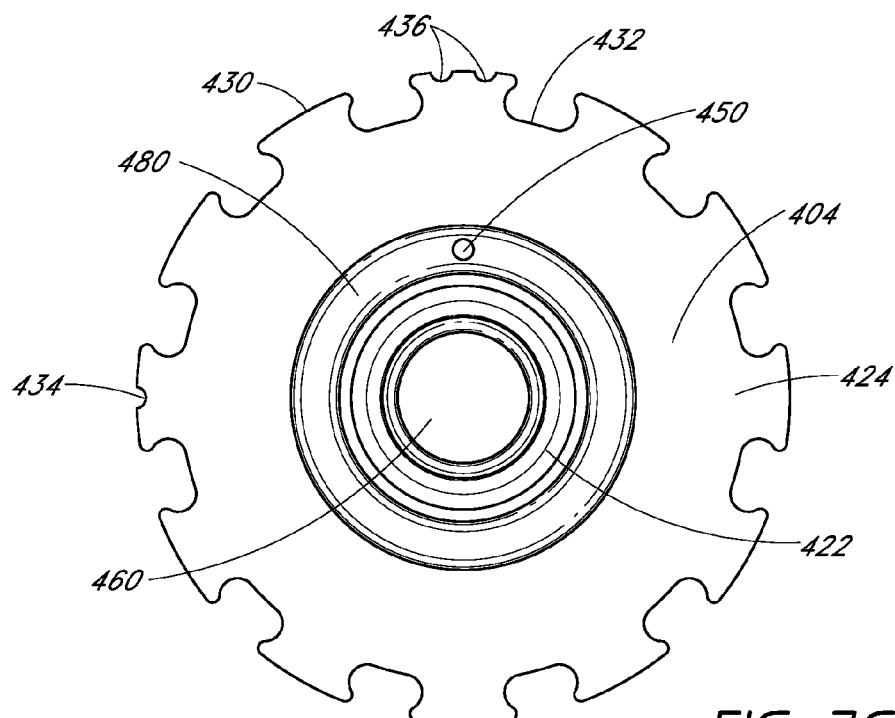
FIG.7C is a back view of the flow controller of FIG.7A.
Figure 8:
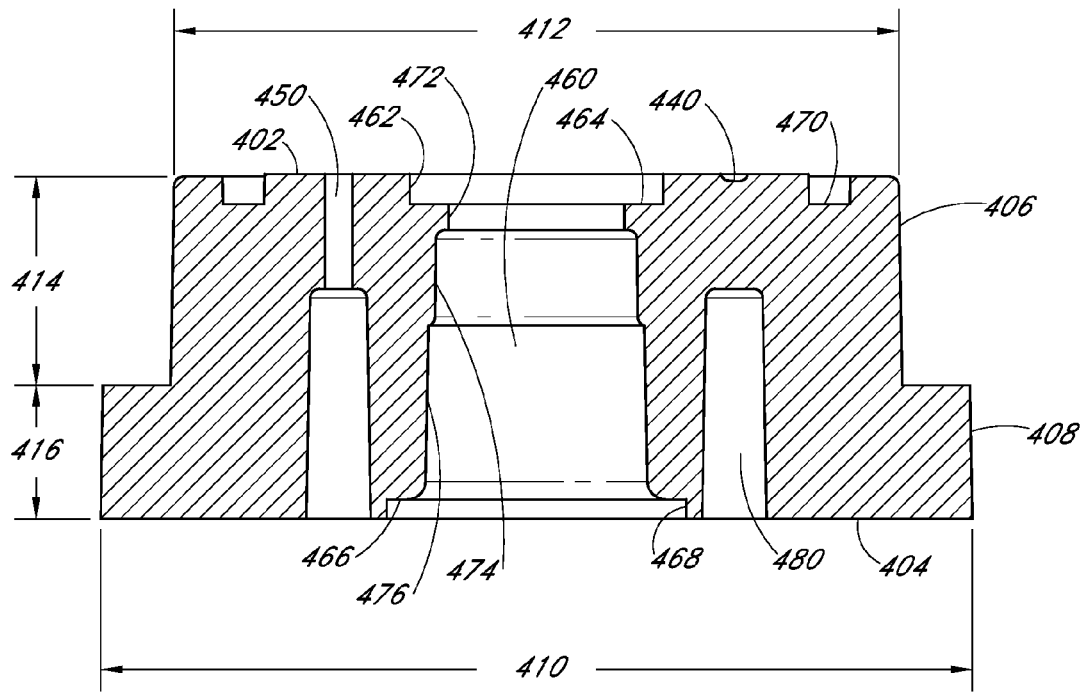
FIG.8 is a cross section of the flow controller of FIG.7B taken along lines 8-8.

With reference next to FIGS. 7A through 7C and 8, an embodiment of a flow controller 400 is illustrated. The flow controller 400 has a first face 402 and an opposing second face 404. A view of the first face 402 is illustrated in FIG. 7B and a view of the second face 204 is illustrated in FIG. 7C. A cross section of the flow controller is illustrated in FIG. 8.

The flow controller 400 has a generally circular shape with a plurality of regions of varying widths and thickness. In this embodiment there is a first region 406 having a width 410 and thickness 414; and a second region 408, having a width 412 and thickness 416. The outer wall 418 of the first region 406 is substantially smooth; and maintains a substantially constant thickness 414 and width 410, which extends substantially between the first face 402 and the second region 408, resulting in a step-type structure where the regions meet. The second region 408 has a plurality of lobes 430 with a corresponding inward shaped cavity 432. The flow controller 400 further comprises a first annular groove 470, a second annular groove 480, a variable groove 440, a through hole 450, and a mounting hole 460. In the illustrated embodiment these structures of the flow controller 400 are positioned similarly and function similarly to the structures identified in connection with the flow controller 200 discussed above.

With specific reference to FIG. 8, the mounting hole 460 of the illustrated flow controller 400 comprises a sealing wall 462, a first recessed face 464, a first inner wall 472, a second inner wall 474, a third inner wall 476, a second recessed surface 466, and an adapter wall 468. The sealing wall 462 extends inwardly from the first face 402 and transitions into the recessed face 464, resulting in a step-type structure. The adapter wall 468 extends inwardly from the second face 404 and transitions into the second recessed face 466, resulting in a step-type structure. The first inner wall 472 extends between the recessed face 454 and the second inner wall 474. The second inner wall 474 extends between the first inner wall 472 and the third inner wall 476. The third inner wall 476 extends between the second inner wall 472 and the second recessed face 466. In this embodiment the inner walls, sealing wall, and adapter wall are circular and concentric. The recessed face 464, sealing wall 462, and first inner wall 472 are sized and configured such that a sealing member, such as an o-ring, can fit between the first inner wall 472 and the sealing wall 462 without substantially obstructing the cavity created by the first inner wall 472. In the illustrated embodiment of the flow controller 400 the mounting hole 460 is configured to accommodate a threaded valve stud adapter 500.

With particular reference to FIGS. 9A, 9B and 10, an embodiment of a valve stud adapter 500 is illustrated, which comprises a valve stud engagement region 510, a manifold engagement region 520, an annular ring 530, and an inner wall 540. The inner wall 540 defines an internal passage that extends through the length of the adapter 500.

The valve stud engagement region 510 has an interior threaded region 514, defining a female connection, and a flange 512 with opposing first and second faces 516, 518. The annular groove 530 is formed along the exterior of adapter 500. Preferably the annular groove 530 is configured to accommodate a sealing member 360e, such as an o-ring. The manifold engagement region 520 has an exterior threaded region 522, defining a male connection.

With specific reference now to FIG. 9A, the flow controller 400, valve stud adapter 500 and sealing members 360 are illustrated. When assembled, the flow controller 400, valve stud adapter 500 and the plurality of sealing members 360 are coupled together. The first annular groove 470 on the flow controller 400 is configured to accommodate the sealing member 360a. The mounting hole 460 is configured to accommodate the sealing member 360b between the sealing wall 462 and the inner wall 472. The sealing member 360b generally abuts the first recessed face 464 and the sealing wall 462 when coupled to the flow controller 400. Preferably the sealing members are elastomeric members of standard sizes and shapes, such as o-rings. The annular groove 530 on the adapter 500 is configured to accommodate the sealing member 360e.

With particular reference to FIGS. 6, 9B, and 10, the assembly of a valve station 330 is illustrated. The valve station 330 comprises the flow controller 400, valve stud adapter 500, valve 340, and manifold 310. This portion of the manifold 310 comprises a non-countersunk valve engagement region 312, a valve station inlet 314, and a valve station outlet 316. The valve station inlet 314 communicates with an inlet passage 326 and an inlet galley 324. The valve station outlet 316 communicates with an outlet passage 322 and an outlet galley 320. The illustrated manifold 310 has similarities in structure and function to the manifold 110 identified in connection with FIGS. 1, 4B, and 5 discussed above.

The valve comprises a valve body 342, a valve interface 344, a valve stud 346, and a valve inlet 348. The valve interface 344 further comprises a plurality of annular grooves designed to accommodate the sealing members 360c and 360d. The valve stud 346 extends outwards from the valve interface 344. The valve stud has an interior cavity that extends from the distal end of the valve stud 346 into the valve body 342 and is in fluid communication with the valve inlet 348. Preferably, the valve stud 346 has an externally threaded region, thus defining a male connection.

The valve station is assembled by coupling the valve 340, valve stud adapter 500 and the manifold 310 with the flow controller 400. In the illustrated embodiment, the adapter 500 is configured to couple with the flow controller 400 through the mounting hole 460. The manifold engagement region 520 extends through the mounting hole 460 such that the distal end extends beyond the first face 402 of the flow controller 400. The first face 516 of the flange 512 is configured to abut the second recessed face 466 of the flow controller 400. The flange 512, second recessed face 466, and adapter wall 468 are sized and configured such that the second face 518 of the flange 512 is flush with the second face 404 of the flow controller when the adapter 500 and flow controller are coupled together. The annular groove 530 of the adapter 500 and sealing member 360e are configured to create a seal between the adapter 500 and the second inner wall 474 of the flow controller 400.

In the illustrated embodiment, the valve is a typical, off-the-shelf type of valve, and the length of the valve stud 346 is not sufficiently long to extend fully through the flow controller 400 and engage the manifold outlet passage 322. To ameliorate this insufficiency, the valve stud adapter 500 is configured to threadingly couple to the valve stud 346 so as to effectively lengthen the stud. The externally threaded region of the valve stud 346 engages the internally threaded region 514 of the valve stud adapter engagement region 510. The adapter 500 is threaded onto the valve stud 346 until it is sufficiently tight to create a seal between the sealing member 360c and the second face 518 of the adapter flange 512.

The distal end of the valve stud adapter 500 extends through the mounting hole 450 of the flow controller 400 and protrudes beyond the first face 402 of the flow controller 400. In this embodiment, the second face 404 of the flow controller 400 abuts the valve interface 344 when the valve station 320 is assembled. In some embodiments there may be a gap between the second face 404 and the valve interface 344.

The manifold engagement region 520 of the valve stud adapter 500 is configured to threadingly couple with the manifold outlet passage 322. The male threaded region 522 of the valve stud adapter 500 engages the female threaded region of the outlet passage 322. Preferably a sealing member, such as Teflon tape, is applied to the threaded region 522 of the valve stud adapter 500 before it is threaded into the manifold outlet passage 322 to help form a seal between the valve 340 and the manifold 310. The valve 340 is then threaded sufficiently tight so that the sealing members 360 form seals between the valve interface 344 and the second face 404 of the flow controller 400, and between the first face 402 of the flow controller 400 and the manifold engagement region 312. When the manifold 310 and the flow controller 400 are coupled together the valve engagement region 312 engages the first face of the flow controller 402. In some embodiments there may be a gap between the valve engagement region 312 and the first face 402.

The sealing members 360b and 360e cooperate to create a seal isolating the valve stud adapter 500 from the inlet passage 326 and further prevent leakage. The sealing member 360a creates a seal isolating the manifold inlet passage 326 and the variable groove 440 from the ambient air and further prevents leakage. In some embodiments there may be a gap between the second face of the flow controller and the valve interface. The sealing member 360d contacts and creates a seal between the second face 424 of the flow controller 400 and the valve interface 344. The outer seal isolates the valve inlet 348 from ambient air and prevents leakage. When the valve 340 and flow controller 400 are assembled, the variable groove 440 and null zone 448 are preferably aligned with the manifold inlet passage 326 such that the inlet passage 326 is in fluid communication with either the variable groove 440 or the null zone 448 regardless of the angular position of the flow controller 400. The second annular groove 480 is preferably aligned with the valve inlet 348 such that the valve inlet 348 remains in fluid communication with the second annular groove 480 regardless of the angular position of the flow controller 400. Preferably the seals 360 cooperate to isolate fluid flow between the inlet port 314 and outlet port 316.

Preferably, the valve 340 is tightened onto the manifold 310 sufficient to establish a reliable seal, but not to the extent that rotational movement of the flow controller 400 is substantially inhibited. Preferably, the flow controller 400 has freedom to rotate about a center axis when urged to do so by a user. Preferably the seals 360 between the flow controller 400, valve 340, valve adapter 500, and manifold 310 are maintained during such movement.

Generally, the use of a valve stud adapter enables standard valves with standard-sized studs to be used with the flow controller and the manifold without customizing of the manifold to accommodate different valves. Also, it should be understood that other sizes, shapes, and specific structures of stud adapters may be employed. For example, in another embodiment a stud adapter is configured to lengthen the valve's original stud, but with little or no interaction with the flow controller, and as such a controller such as the flow controller 200 discussed above can be used.

The flow control system 300 and valve station 320 preferably operate following the same general principles of the flow control system 100 and valve station 120 described in connection with FIGS. 1, 4B, and 5, detailed above.

Figure 11:
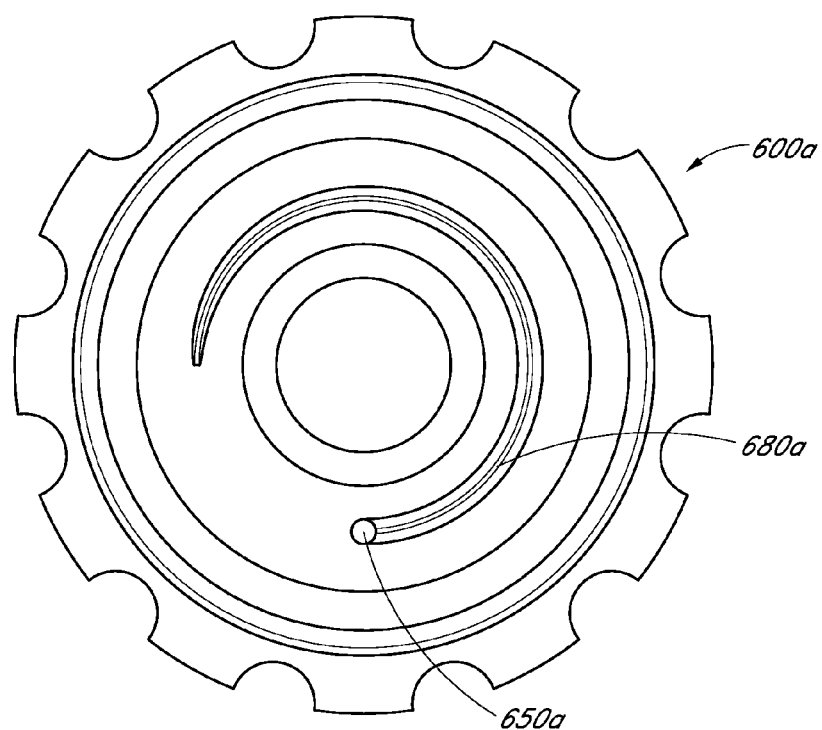
FIG.11 is a front view of one embodiment of a flow controller with a smaller groove.
Figure 12:
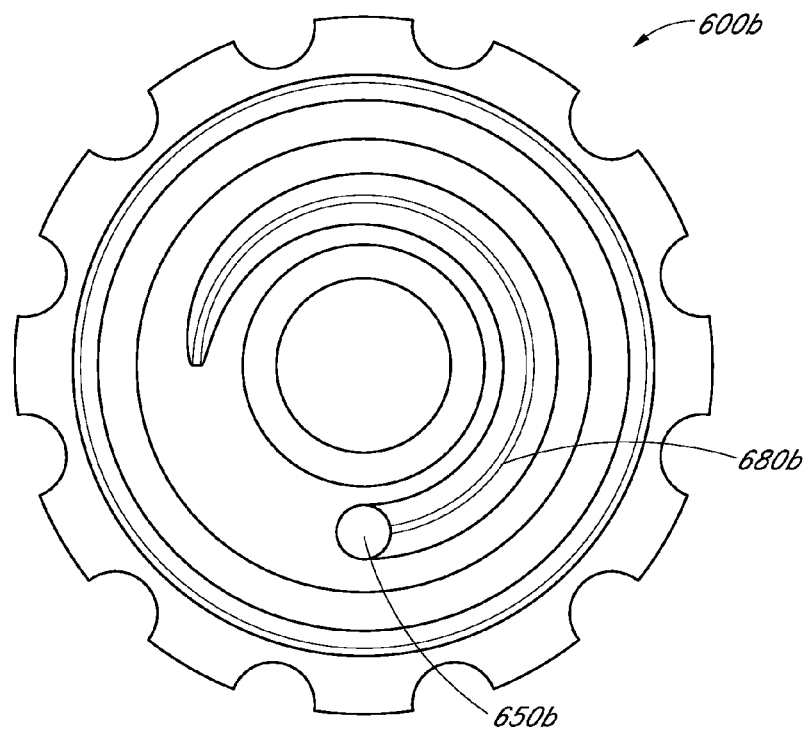
FIG.12 is a front view of one embodiment of a flow controller with a larger grove.

FIGS. 11 and 12 illustrate additional embodiments of flow controllers 600a, 600b with different variable grooves. The flow controllers 600a, 600b contain the same general structure discussed in association with the flow controller illustrated in FIGS. 2 and 3. FIG. 11 illustrates a narrower variable groove 680a and a smaller diameter through hole 650a. FIG. 12 illustrates a wider variable groove 680b and larger diameter through hole 650b. Preferably the size of the through hole determines the maximum flow rate of the flow controller during operation of a flow control system. The maximum flow rate increases as the diameter of the through hole increases. For example a smaller diameter through hole of 0.032" will flow a maximum of about 12 SLPM, whereas a larger diameter through hole of 0.059" will flow a maximum of about 35 SLPM. Thus, assembling flow controllers of different ranges to identical valves and manifolds results in flow assemblies having different ranges of flow rates.

As illustrated by the embodiments in FIGS. 11 and 12, modifying the size and shape of the through hole and variable groove can significantly change the range of fluid flow rates of the flow controller. The length, depth, width, and shape of the groove can be modified and changed to fit the needs of the specific application of the flow controller. Different flow controllers can change the effective flow rate range of standard-sized valves. As such valves can be effectively customized without physically modifying the valve.

The material of the controller can be any material that is needed for the specific application, for example metal, rubber, plastic or other suitable material can be used to fabricate the flow controller. In the preferred embodiment, the flow controller is made of plastic.

Figure 13A:
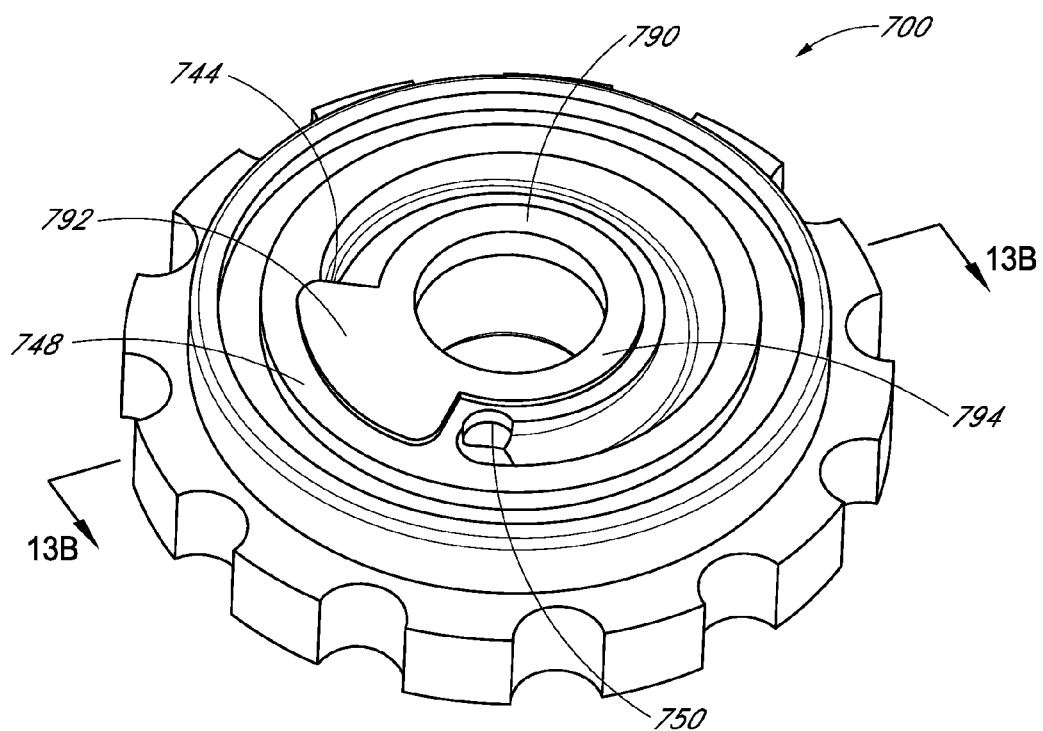
FIG.13A is a perspective view of one embodiment of a flow controller with two materials.
Figure 13B:
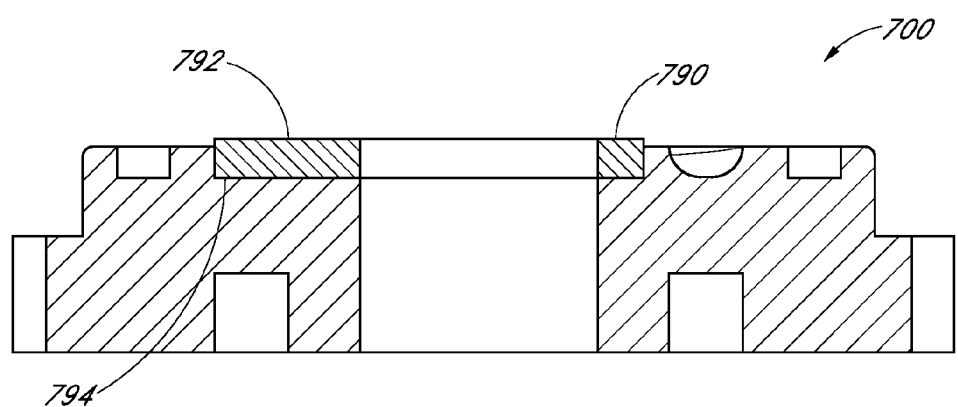
FIG.13B is a cross section view of the flow controller of FIG.13A.

FIGS. 13a and 13b illustrate another embodiment of a flow controller 700 that comprises an insert 790 made of a material that is softer than the material used to fabricate the flow controller 700. The insert comprises a central portion 794 and a tab 792. The insert 790 is a separate component that is coupled to the flow controller 700 in an engagement region 794. In the illustrated embodiment, the majority of the flow controller is formed of a hard plastic but the insert is an elastomeric material and the central portion 794 forms a seal with a valve stud and manifold when assembled in a valve station. The tab 792 extends into the area between a through hole 750 and a second end of a variable groove 744, which area is a null zone 748. In this embodiment, the soft material of the tab 792 creates a seal with a fluid inlet, thus decreasing the airflow until it is virtually nonexistent or, in some embodiments, creating a full seal. In this embodiment the insert is raised slightly relative to the surrounding surface of the flow controller. In some embodiments the insert may be flush with the face of the flow controller. In other embodiments the flow controller may not have an engagement region and the insert has a stepped tab, where the central portion engages the mounting hole and the tab abuts the face of the flow controller.

Figure 14:
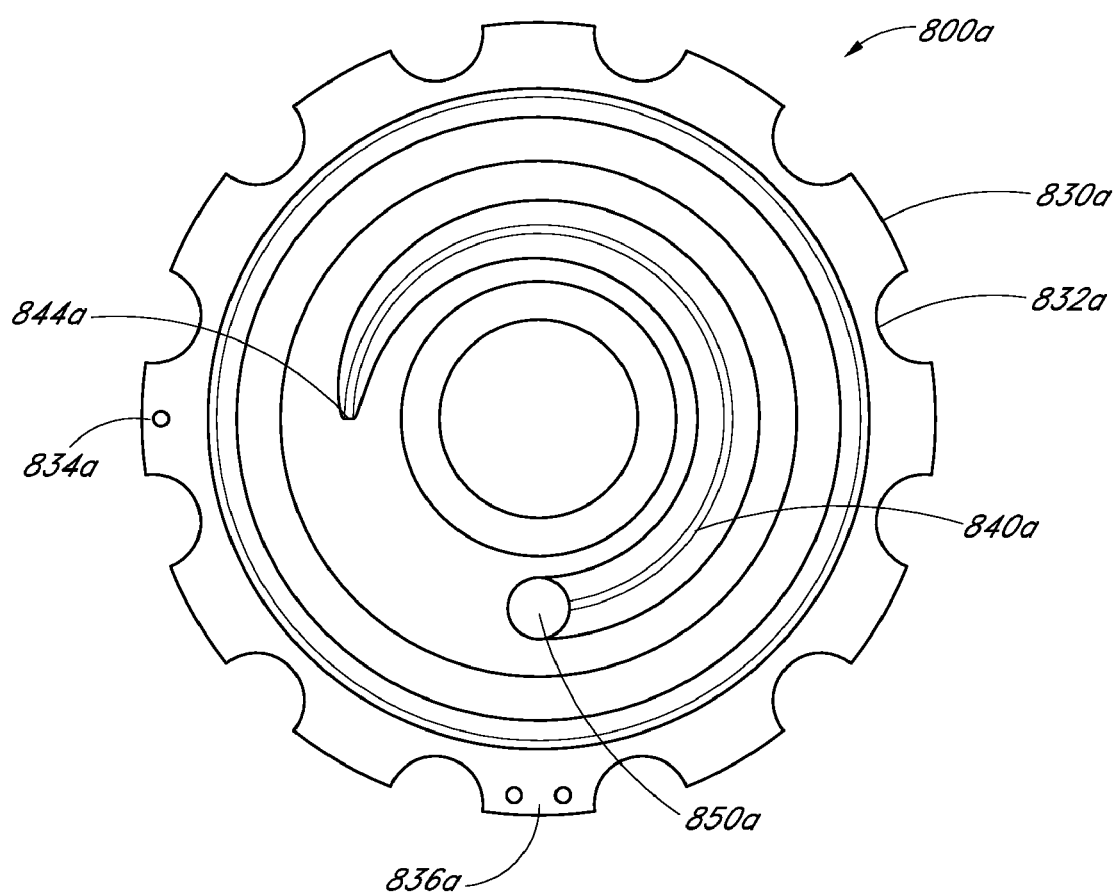
FIG.14 is a view of one embodiment of a flow controller with one embodiment of lobe markings.
Figure 15:
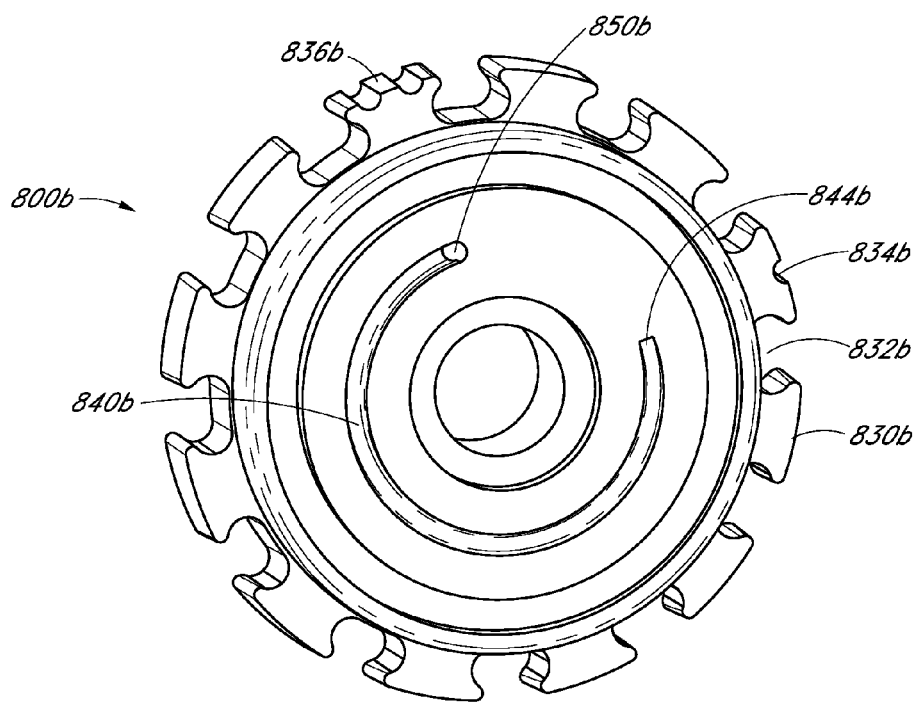
FIG.15 is a view of one embodiment of a flow controller with another embodiment of lobe markings.

FIGS. 14 and 15 illustrate additional embodiments of flow controllers 800a, 800b with varied lobes 830a-b and markings 834a-b, 836a-b. In these embodiments, the lobes 830a-b along the edge have markings which designate when a desired flow is reached, such as minimum or maximum flow. In FIG. 14 the markings 834a, 836a are holes, in FIG. 15 the markings 834b, 836b are notches. In other embodiments the lobes may have other types of markings. Any number of lobes 830 may be marked. For example, additional lobes may be marked to indicate specific flow rates.

In the embodiment in FIG. 14, the lobe opposite a second end 844a of the variable groove 840a is marked with a single hole 834a, which is visible to the operator to show when minimum flow is reached. The lobe opposite the through hole 850a is marked with two small holes 836a to show when the through hole is lined up with the fluid inlet and maximum flow is achieved. In some embodiments the markings are visible on both sides of the flow controller. In other embodiments the markings may only be visible on one side of the flow controller. The embodiment illustrated in FIG. 15 uses a similar marking scheme. Maximum flow is marked by two semicircle notches 836b opposite the through hole 850b and minimum flow is marked by a single semicircle notch 834b opposite the second end 844b of the variable groove 840b.

In some embodiments there may be additional marking that designate other points of desired flow. In some embodiments the markings will be printed onto the flow controller. Markings can also correspond to particular flow rates or settings. The flow controller may have an accompanying table that informs the user of flow rates of particular settings for particular fluids and pressures.

In some embodiments the plurality of lobes will differ substantially in shape from the lobes illustrated in the flow controllers illustrated herein, such differences do not depart form the principles of the invention. In some embodiments the flow controller may be configured so that it can be manipulated by a computer control system, gear, or other configuration that is designed to adjust the fluid flow rate by manipulating the flow controller.

Figure 16:
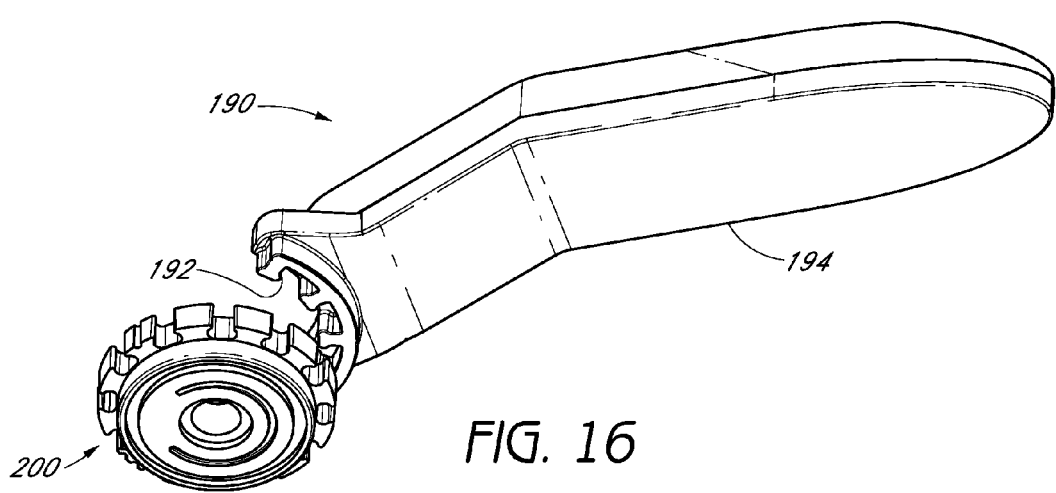
FIG.16 is a perspective view of a flow controller and a tool for manipulating the flow controller disc.

FIG. 16 illustrates a tool 190 specially designed for manipulating a flow controller 200 in a flow control system. In this embodiment the tool comprises a lobe engagement region 192 and a handle 194. The lobe engagement region 192 is designed to be a mirror image of a plurality of lobes 230 and corresponding inward regions 232 on the flow controller 200. Preferably the number of lobe engagement regions will vary dependent on the size and nature of the flow controller. The tool is used to rotate the flow controller to the desired position in order to achieve a desired flow rate. Preferably the lobe engagement region will engage with the plurality of lobes 230 and facilitate the precise rotational movement of the flow controller 200. The tool is particularly helpful when a valve station is assembled and the valve is screwed into the manifold such that the flow controller does not self rotate. The tool provides additional torque and enables precise adjustments of the flow controller, thus allowing the user to precisely control the flow rate.

Figure 17:
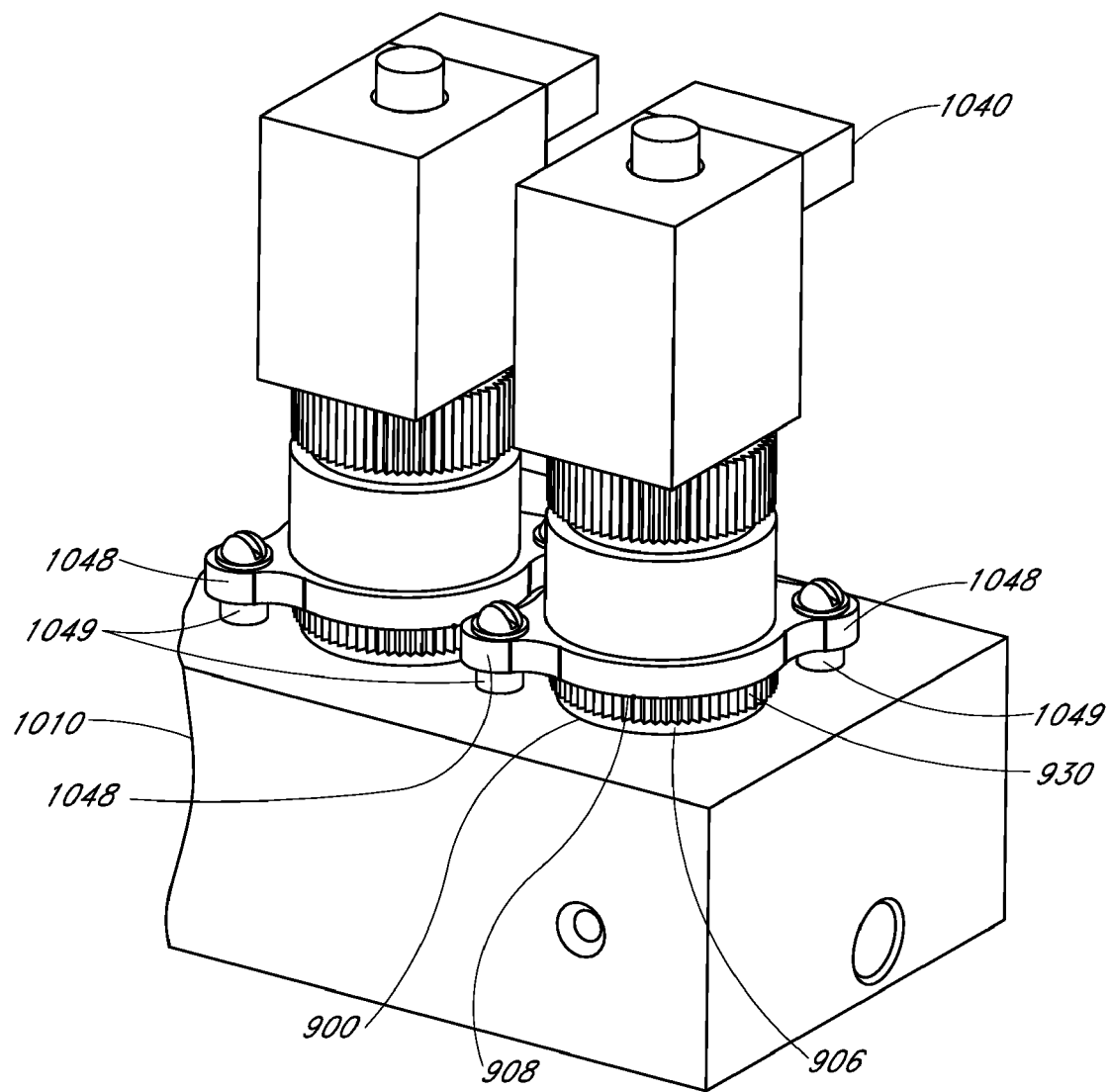
FIG. 17 is a perspective view of another embodiment of a flow control system.

FIG. 17 shows another embodiment of a flow controller 900 which is adapted for use with a valve 1040 that does not have a central valve mounting stud. The valve 1040 is mounted on a manifold 1010 or sub-plate using external ears 1048 instead of a centrally-located valve mounting stud. In some embodiments a stand-off 1049 may be added to each ear 1048 to bridge across the flow controller 900. Preferably, the flow controller 900 has a structure employing similar principles to the flow controller 200 described herein in association with FIGS. 2 and 3, specifically with regards to the structures employed on the first and second faces of the flow controller 200, and in particular including a tapered groove leading to through-hole.

In the illustrated embodiment the flow controller 900 has a first region 906 and a second region 908 with similar diameters. The second region has a knurled area 930 along its outer edge. Preferably, the knurled edge is configured such that it can be manipulated without interference from the standoffs 1049. This embodiment may be used to accommodate a larger-footprint valve.

The operation of the flow controller 900 follows the same general principles of operation described herein in association with other embodiments of the flow controllers. The primary difference is the method of mounting the valve to the manifold. The principles embodied in the flow controller are not limited to a single type of valve or manifold structure and may be applied to all types of fluid control systems.

The embodiments discussed above describe flow controllers that are generally circular and which rotate about a central axis. In other embodiments, the configuration of the flow controller may vary to accommodate the geometry of the application, as the flow controller used with the valve of FIG. 17 is structurally different than the flow controller used with the valve of FIGS. 1 and 6. It should be appreciated that other valve types, and in fact other flow control situations in which a flow controller may or may not directly interact with an associated valve or manifold, may use flow controller embodiments that employ the principles discussed herein but have sizes and specific shapes that vary from the embodiments specifically disclosed herein. For example, in some embodiments the flow controller may be generally linear, in which the flow controller has a linear rather than arcuate variable groove, and the controller is moved along a generally linear path to adjust the alignment with a flow source and thus the flow rate.

Additionally, in some embodiments, the flow direction through the controller can be opposite the direction as shown in the embodiments specifically discussed above. Further, although embodiments discussed herein have depicted flow controllers with both and input flow path and an output flow path through the controller, it is anticipated that in some embodiments a flow controller will have only one flow path therethrough, and interact with only an input or output side of a fluid flow path. However, such a flow controller may still employ a variable cross-section groove configuration that selectively limits flow.

Applicants contemplate that further applications may employ the principles discussed herein in other ways. For example, in some embodiments a valve may be modified so that a flow controller is incorporated as part of the valve. Or in other embodiments a flow controller may be incorporated as part of the manifold. In still other embodiments, a flow controller can be interposed in a flow path substantially independent of any manifold or valve.

It is thus to be understood that the embodiments set forth above are illustrative of inventive principles and features, and these principles may be applied to variable tracks or grooves that are circular, linear, or follow a specified path. As such, the principles and features discussed herein can be applied in embodiments of various shapes, sizes and configurations.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, in another embodiment, flow controller 200 can be constructed without a second annular groove 280. It is also contemplated that various combinations or subcombinations of the specific features and aspects of the embodiments may be made and still fall within the scope of the invention. For example, the flow controller structure including a relatively soft insert 790 can be incorporated into other embodiments, such as flow controllers 200, 400, 600*a*, 600*b*, 800*a*, 800*b*, 900, and other additional embodiments and structures as just discussed. Accordingly, Applicants contemplate that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A flow control system, comprising:
   a manifold comprising a manifold fluid inlet and a manifold fluid outlet;
   a valve comprising a valve fluid inlet, a valve fluid outlet, and a mechanism for controlling when fluid flows therethrough;
   a flow controller detachably coupled to the valve, the flow controller comprising
      a body having a first side and a second side;
      an elongate groove on the first side of the body, the groove having a first end and a second end, a cross-sectional area of the groove increasing from the second end toward the first end;
      an annular groove on the second side of the body; and
      a hole through the body at the first end of the elongate groove, the hole extending to the annular groove;
   wherein the flow controller is interposed between the valve and manifold;
   wherein the annular groove is configured to align with the valve fluid inlet;
   wherein a fluid flow path conveys a fluid from the manifold through the fluid inlet, the flow controller, the valve fluid inlet and into the valve;
   wherein the flow controller is rotatable relative to the manifold and the valve from a first position in which a first portion of the annular groove is aligned with the fluid inlet to a second position in which a second portion of the annular groove is aligned with the fluid inlet;
   wherein the cross-sectional area of the groove at the first portion determines a first flow rate when the flow controller is in the first position and the cross-sectional area of the groove at the second portion determines a second flow rate when the flow controller is in the second position; and
   wherein the first flow rate is different than the second flow rate; and
   wherein the valve fluid inlet remains in fluid communication with the annular groove as the flow controller rotates from the first position to the second position.

2. The system of claim 1, wherein substantially all of the fluid flow passes through the hole in the flow controller.

3. The system of claim 1, wherein the system further comprises a valve stud adapter having a valve engagement region, a manifold engagement region, and an internal passage extending along its length, wherein the valve engagement region couples to the valve and the manifold engagement region couples to the manifold so that the valve stud adaptor internal passage communicates the valve fluid outlet with the manifold fluid outlet.

4. The system of claim 1, wherein the flow controller is movable relative to the manifold to a third position at which the fluid inlet is not aligned with the annular groove, and flow is substantially blocked by the flow controller.

5. The system of claim 3, wherein the flow controller comprises a mount hole spaced from the hole at the first end of the elongate groove, and the stud adaptor fits through the mount hole.

6. A flow controller, comprising:
   a body having a first side and a second side;
   an elongate groove on the first side of the body, the groove having a first end and a second end, a cross-sectional area of the groove increasing from the second end toward the first end;
   an annular groove on the second side of the body, the annular groove having a width and a depth, the depth being substantially the same along the length of the annular groove; and
   a hole through the body at the first end of the elongate groove, the hole extending through the body to the annular groove.

7. The flow controller of claim 6, wherein the elongate groove is continuously tapered in width and depth, such that at the first end the elongate groove is widest and deepest, and at the second end the elongate groove terminates at a point where it becomes generally flush with the body.

8. The flow controller of claim 6, wherein the body is generally circular in shape and has an axis, and the elongate groove is arcuate about the axis.

9. The flow controller of claim 8, wherein the body further comprises at least one annular groove configured to accommodate a sealing member.

10. The flow controller of claim 8, wherein there is an angular space on the first side between the first end and the second end of the elongate groove that is substantially flat, wherein the space is approximately 90 degrees.

11. The flow controller of claim 10, wherein at least a portion of the angular space comprises a different material than the rest of the flow controller, wherein the different material is an elastomeric material.

12. The flow controller of claim 8, wherein the flow controller further comprises a center hole arranged along the axis of the body, the center hole being spaced from the elongate groove and the annular groove and extending from the first face to the second face, wherein the second hole is configured to accommodate a valve stud.

13. The flow controller of claim 6, wherein the body further comprises:
a first section having a first diameter and a first thickness,
a second section having a second diameter and a second thickness, wherein the first diameter and second diameter are different, wherein the first thickness and second thickness are different.

14. The flow controller of claim 13, wherein the second section has a plurality of lobes formed circumferentially about the second section, and at least one of the plurality of lobes has a marking corresponding to a postion on the groove.

15. A method of controlling fluid flow in a manifold, comprising:
providing a manifold having a fluid inlet and a fluid outlet;
providing a valve configured to control when fluid flows therethrough;
interposing a flow controller between the valve and the manifold, the flow controller having a body with a first side and a second side, the second side having an annular grove, the first side having an elongate groove having a first end and a second end, wherein a cross-sectional area of the groove increases from the second end toward the first end, and a hole adjacent the first end of the groove extends through the body to the annular groove on the second side;
supplying a fluid to the manifold, wherein a fluid flow path conveys the fluid from the manifold through the fluid inlet, the flow controller, the valve, and to the fluid outlet;
rotating the flow controller relative to the manifold and the valve from a first position in which a first portion of the annular groove is aligned with the fluid inlet to a second position in which a second portion of the annular groove is aligned with the fluid inlet, wherein the fluid flows at a first fluid flow rate from the fluid inlet to the fluid outlet when the flow controller is in the first position and the fluid flows at a second fluid flow rate from the fluid inlet to the fluid outlet when the flow controller is in the second position, and wherein the first fluid flow rate is different than the second fluid flow rate; and
maintaing fluid communication within the fluid flow path when rotating the flow controller between the first position and the second position.

16. The method of claim 15, wherein the method further comprises moving the flow controller relative to the manifold so that the fluid inlet is aligned substantially with the hole in the flow controller, wherein fluid flows at a third flow rate from the fluid inlet to the fluid outlet, and the third flow rate is a maximum flow rate through the flow controller.

17. The method of claim 15, wherein the method further comprises moving the flow controller relative to the manifold to a fourth position in which the fluid inlet is not aligned with the annular groove, and wherein the fluid flow is substantially blocked by the flow controller when the controller is in the fourth position.

18. The method of claim 15, wherein the valve comprises a valve stud and the flow controller comprises a mount hole, and interposing the flow controller between the valve and manifold comprises extending the valve stud through the flow controller mount hole and connecting the valve stud to the manifold at the manifold fluid outlet.

* * * * *

UNITED STATES PATENT AND TRADEMARK OFFICE
CERTIFICATE OF CORRECTION

Page 1 of 1

PATENT NO. : 8,327,864 B2
APPLICATION NO. : 12/903998
DATED : December 11, 2012
INVENTOR(S) : Ellis et al.

It is certified that error appears in the above-identified patent and that said Letters Patent is hereby corrected as shown below:

In the Specification:

In column 4 at line 57, Change "grove." to --groove.--.

In column 8 at line 15, Change "their" to --there--.

In column 14 at line 7, Change "form" to --from--.

In the Claims:

In column 16 at line 16, In Claim 1, Change "controller,the" to --controller, the--.

In column 16 at line 38, In Claim 3, Change "region,and" to --region, and--.

In column 17 at line 33 (approx.), In Claim 14, Change "postion" to --position--.

In column 17 at line 43 (approx.), In Claim 15, Change "grove," to --groove,--.

In column 18 at line 21, In Claim 15, Change "maintaing" to --maintaining--.

Signed and Sealed this
First Day of October, 2013

Teresa Stanek Rea
*Deputy Director of the United States Patent and Trademark Office*